(12) United States Patent
Yemini

(10) Patent No.: US 11,918,771 B2
(45) Date of Patent: Mar. 5, 2024

(54) CAPSULE FOR VAPORIZATION OF A LIQUID

(71) Applicant: Novomic LTD, Rosh Ha'Ayin (IL)

(72) Inventor: Zvi Yemini, Yaffo (IL)

(73) Assignee: NOVOMIC LTD, Rosh Ha'Ayin (IL)

( * ) Notice: Subject to any disclaimer, the term of this patent is extended or adjusted under 35 U.S.C. 154(b) by 121 days.

(21) Appl. No.: 17/049,994

(22) PCT Filed: Oct. 31, 2019

(86) PCT No.: PCT/IB2019/053068
§ 371 (c)(1),
(2) Date: Oct. 23, 2020

(87) PCT Pub. No.: WO2019/207405
PCT Pub. Date: Oct. 31, 2019

(65) Prior Publication Data
US 2021/0228850 A1   Jul. 29, 2021

(51) Int. Cl.
*A61M 35/00* (2006.01)
*B01D 1/06* (2006.01)
*B01D 1/16* (2006.01)

(52) U.S. Cl.
CPC .............. *A61M 35/00* (2013.01); *B01D 1/06* (2013.01); *B01D 1/16* (2013.01)

(58) Field of Classification Search
CPC .......... A61M 35/00; A61M 2202/0208; A61M 2202/0225; A61M 11/04; B01D 1/06; B01D 1/16; A01M 1/2055; A01M 13/00; A01M 17/00; A45D 19/16; A61L 2209/133; A61L 9/04
See application file for complete search history.

(56) References Cited

U.S. PATENT DOCUMENTS

| | | | | |
|---|---|---|---|---|
| 1,004,087 A * | 9/1911 | Scheinemann | .......... | B01D 1/06 122/32 |
| 1,524,184 A * | 1/1925 | Cuthbert | .......... | B01D 1/06 159/2.3 |
| 5,205,067 A * | 4/1993 | Thomas | .......... | A01M 1/2055 222/83.5 |
| 5,823,179 A * | 10/1998 | Grychowski | ..... | A61M 15/0021 239/338 |
| 9,307,820 B2 * | 4/2016 | Ritterband | ............ | A45D 19/14 |
| 9,427,536 B2 * | 8/2016 | Fang | .................... | A61M 15/06 |

(Continued)

FOREIGN PATENT DOCUMENTS

WO  WO-2017011865 A1 * 1/2017 ............ A61K 31/08

*Primary Examiner* — Christopher P Jones
*Assistant Examiner* — Phillip Y Shao
(74) *Attorney, Agent, or Firm* — Michael J. Feigin, Esq.; Feigin and Fridman LLC

(57) ABSTRACT

A vaporization capsule including a liquid active agent absorbed in or adsorbed to a substrate, which may be operated so as to vaporize the liquid active agent. The vaporization capsule includes a capsule body defining a first volume and a second volume. A first cover sealingly engages the capsule body at a first end thereof. The first cover includes an exterior perimeter, an interior wall including a hollow defined between the exterior perimeter and the interior wall portion, and at least one indentation disposed in the interior wall portion, fluidly connecting the first volume and the second volume via the hollow.

19 Claims, 24 Drawing Sheets

(56) References Cited

U.S. PATENT DOCUMENTS

2010/0206305 A1* 8/2010 Lee .................. A61M 16/12
                                                    128/200.21
2016/0325080 A1* 11/2016 Glynn ................ A61K 33/14
2017/0165461 A1* 6/2017 Yemini ............... A61M 37/00

* cited by examiner

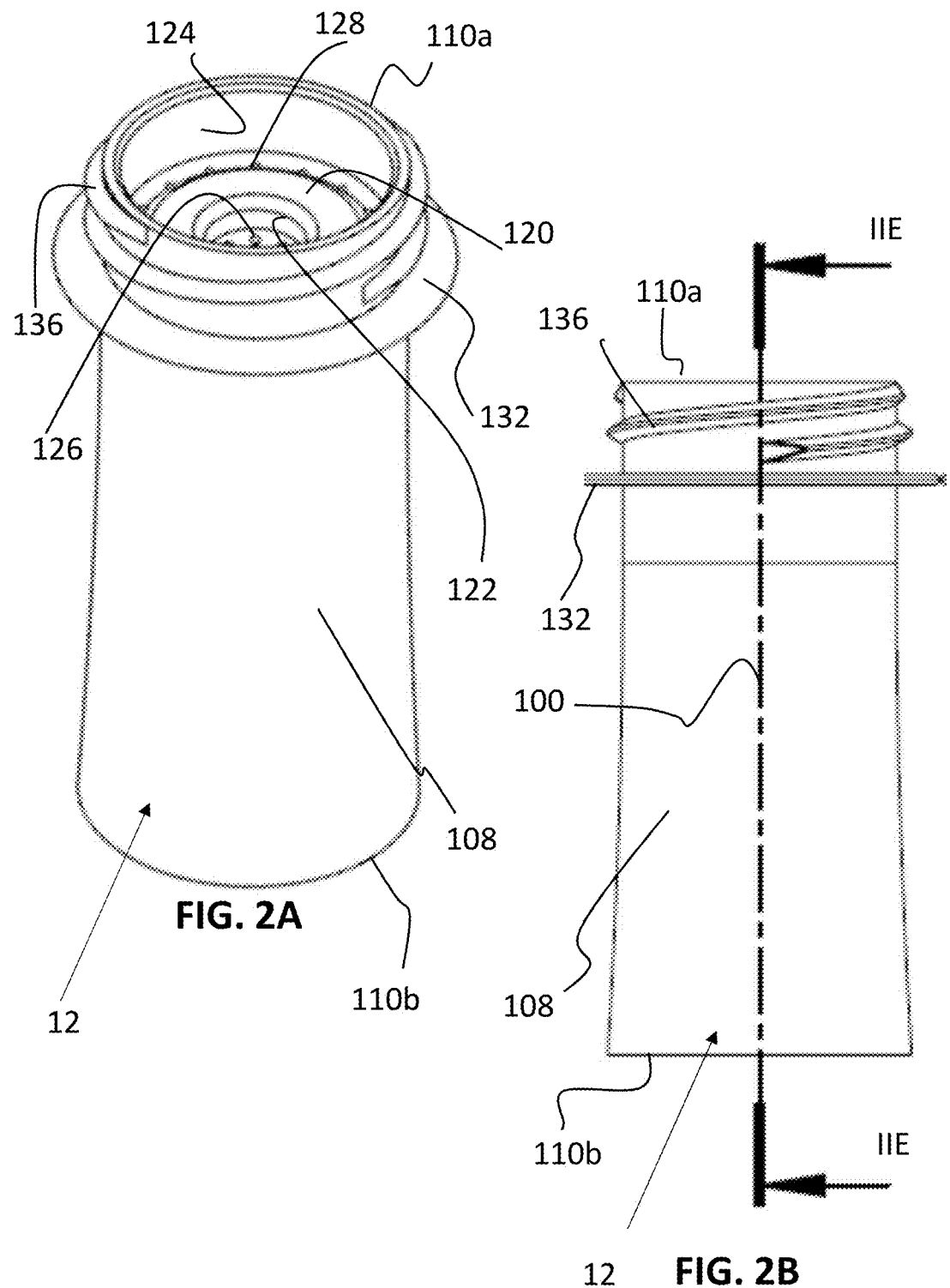

FIG. 2C
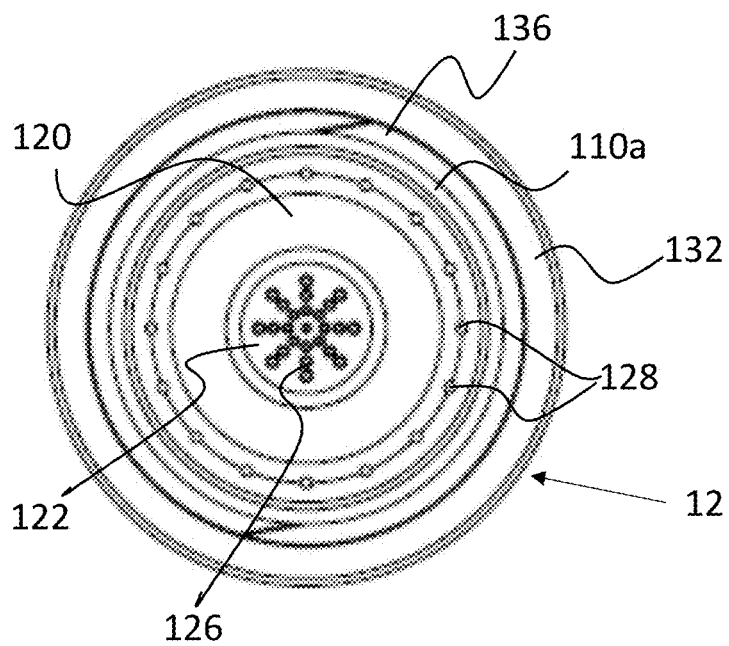
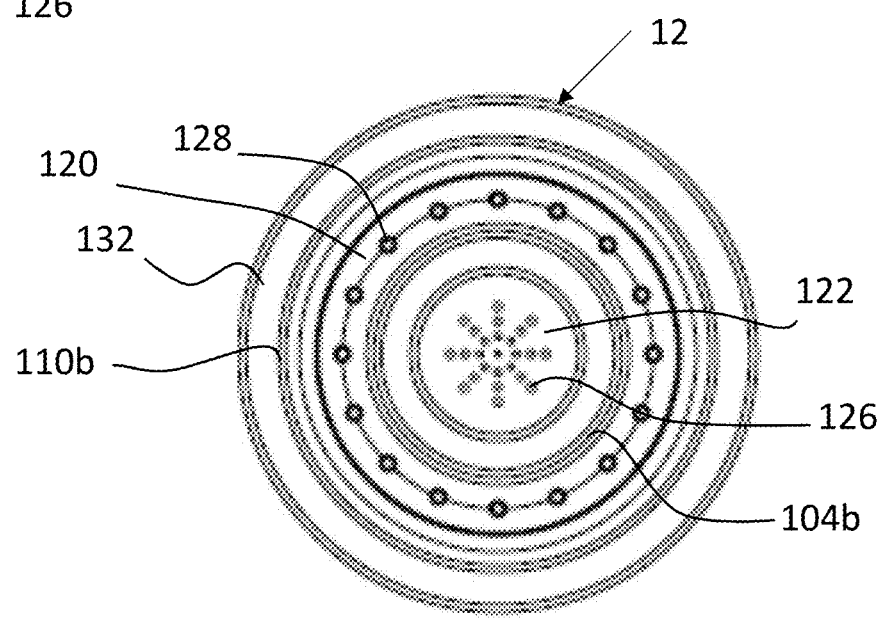
FIG. 2D

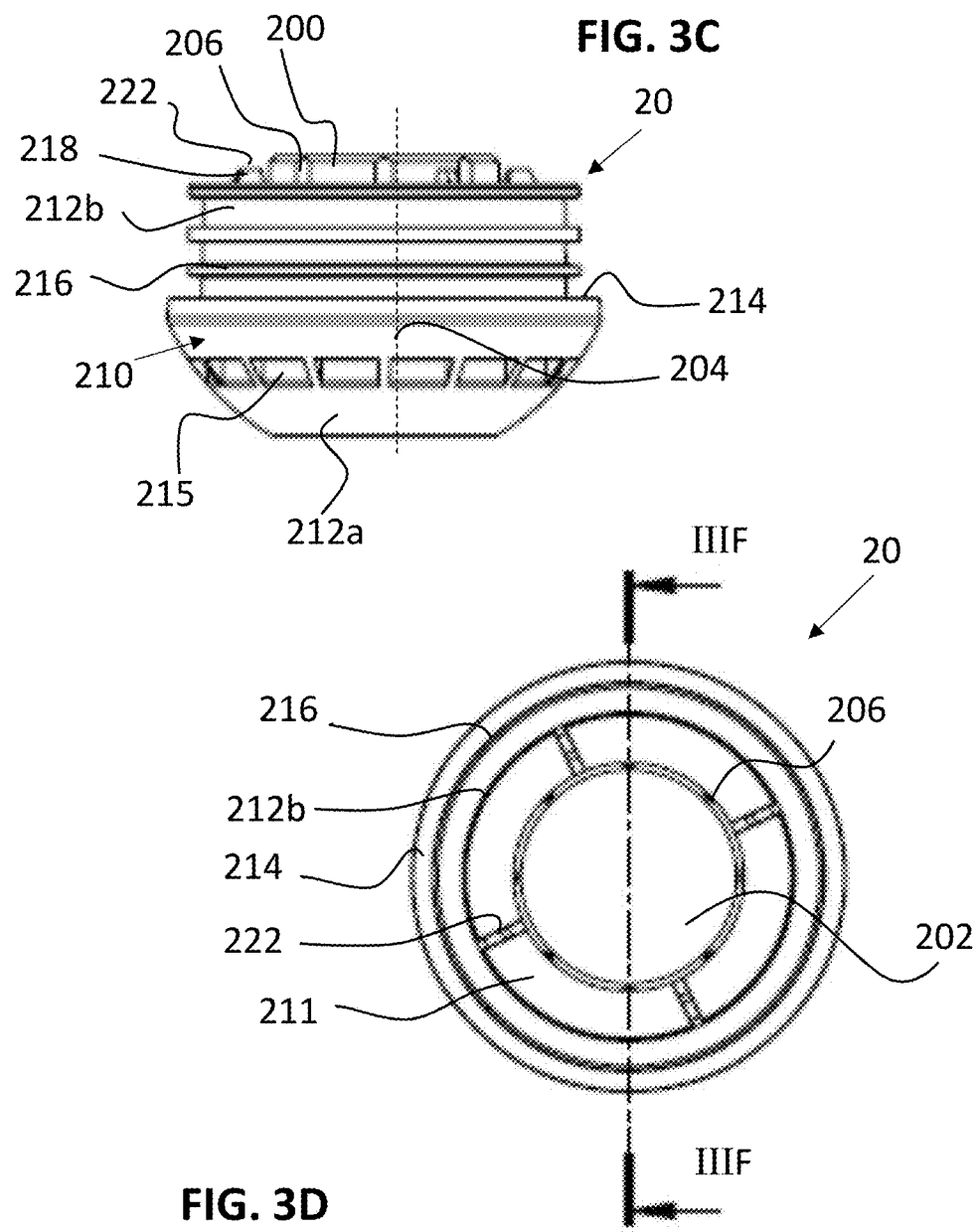

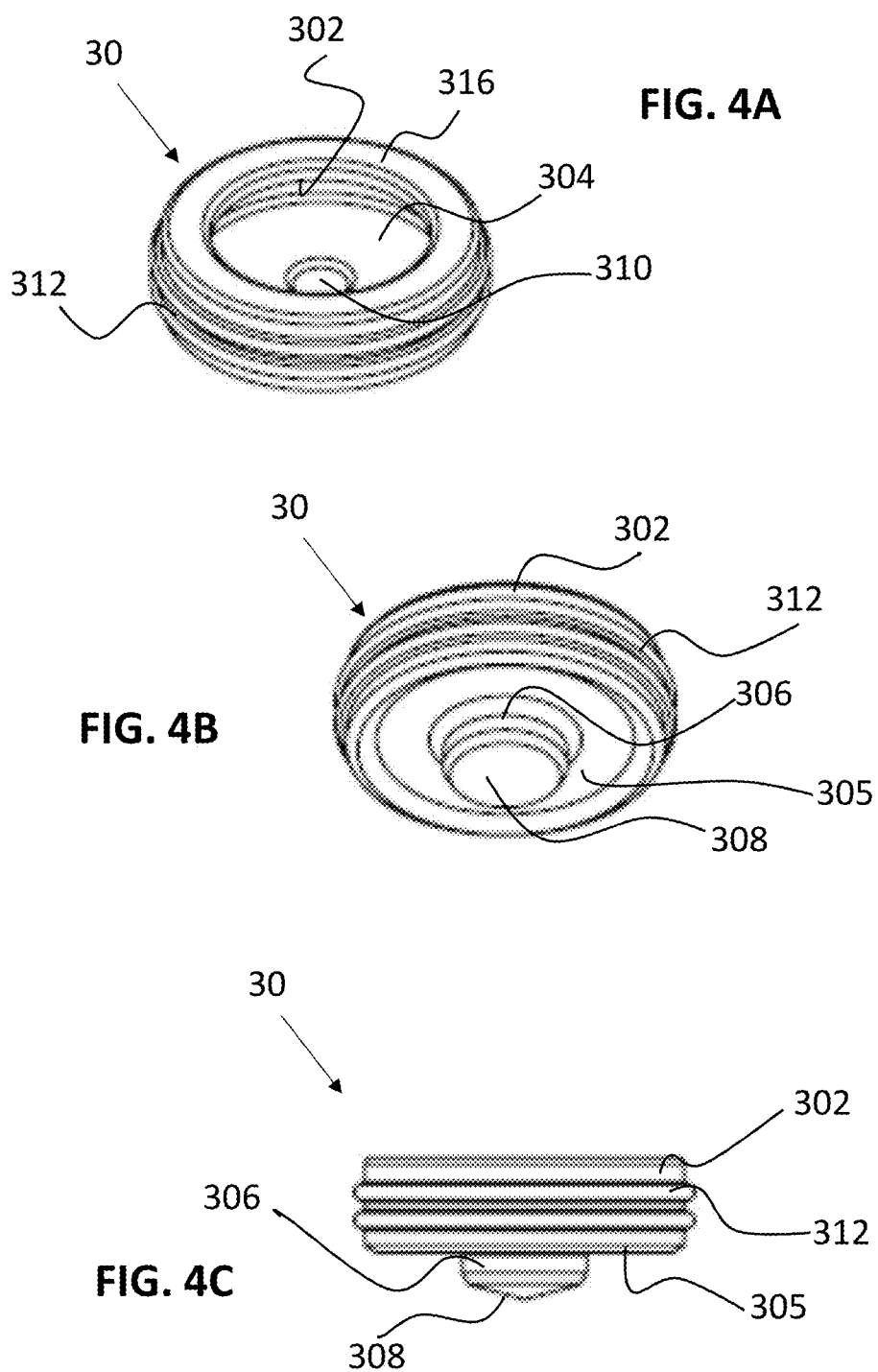

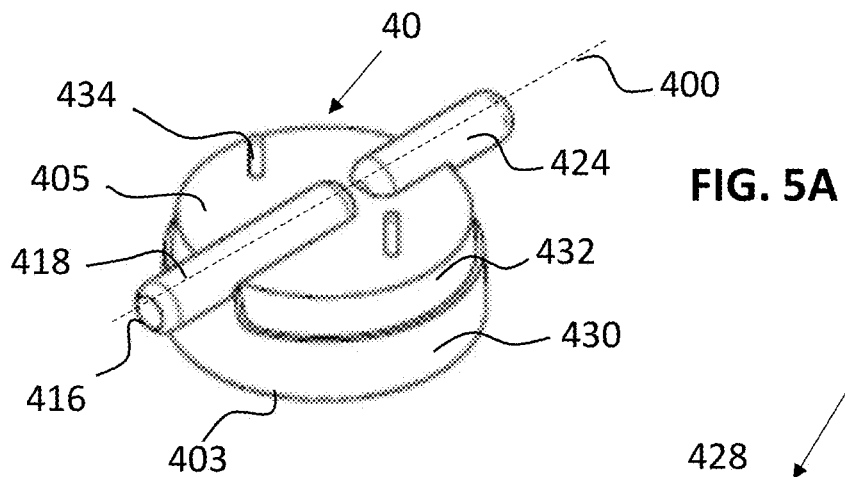
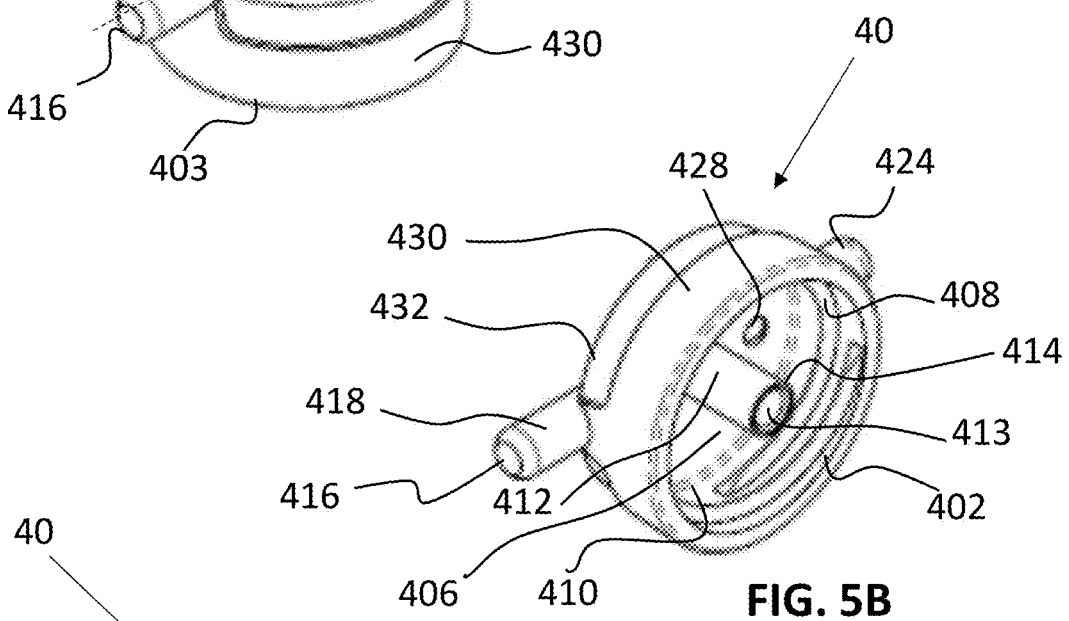
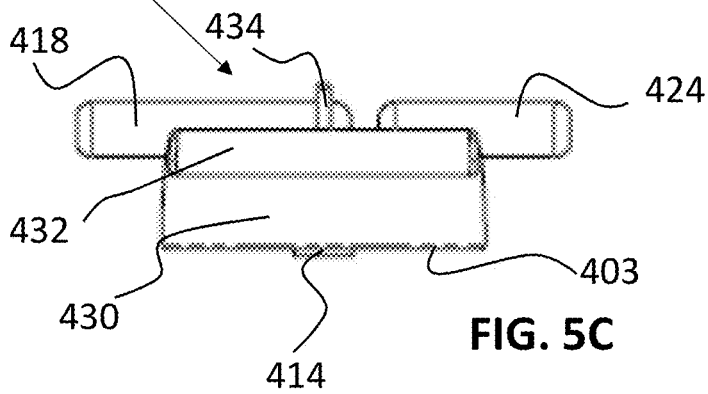

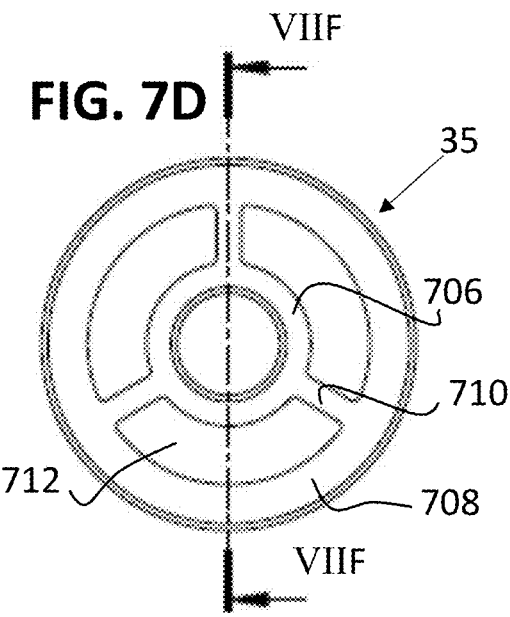
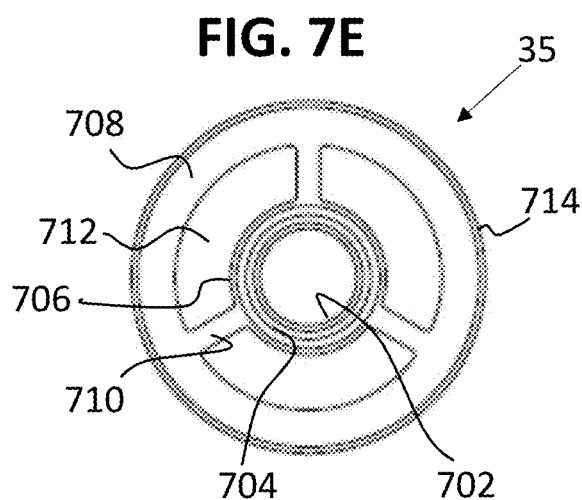
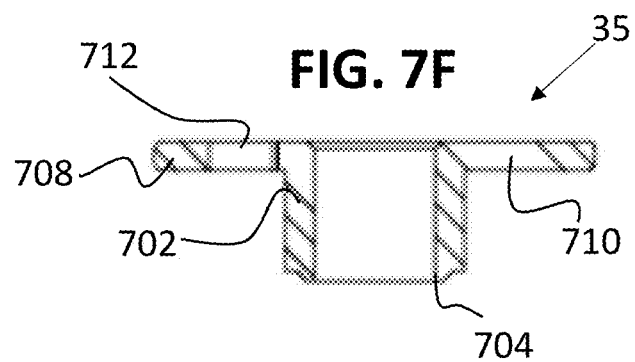

FIG. 8A
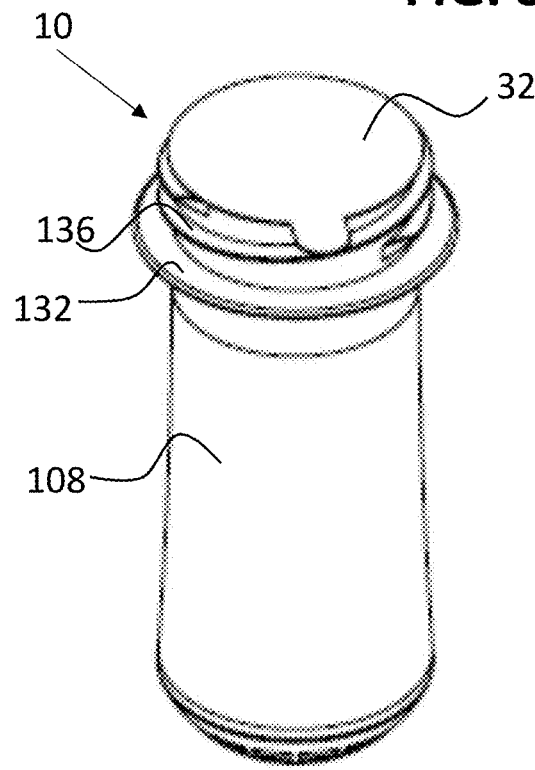
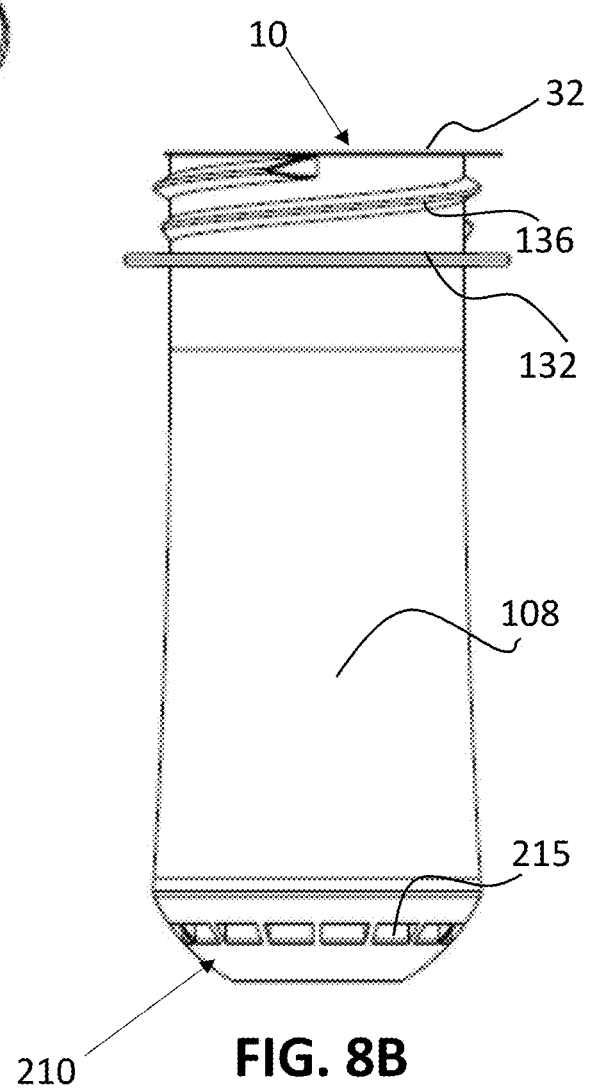
FIG. 8B

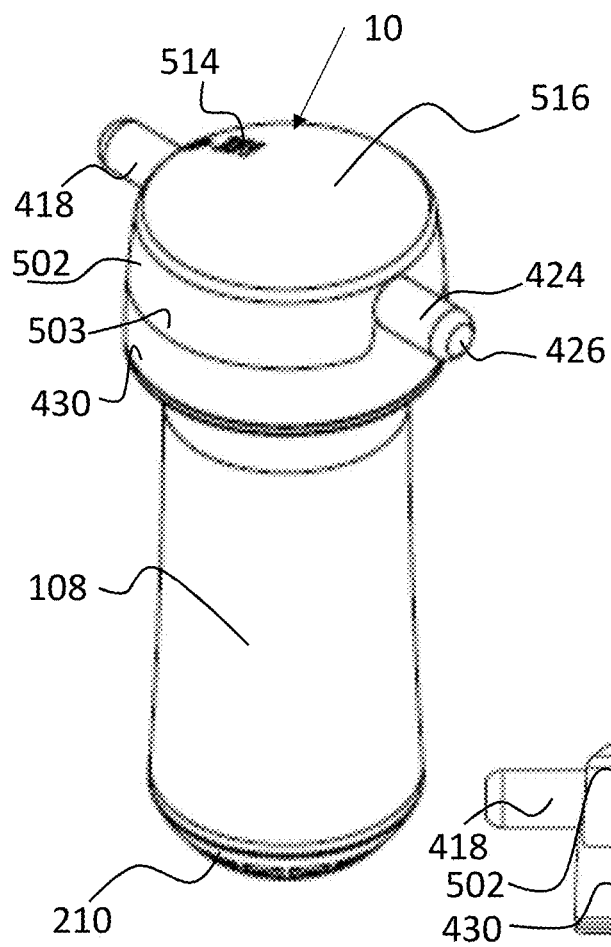
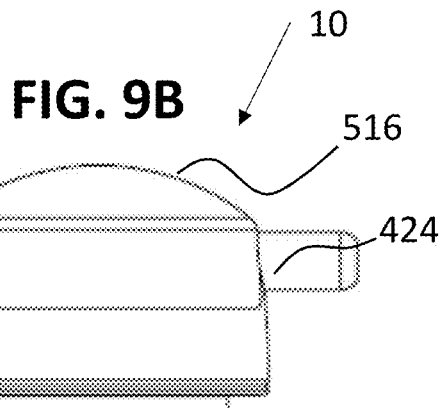
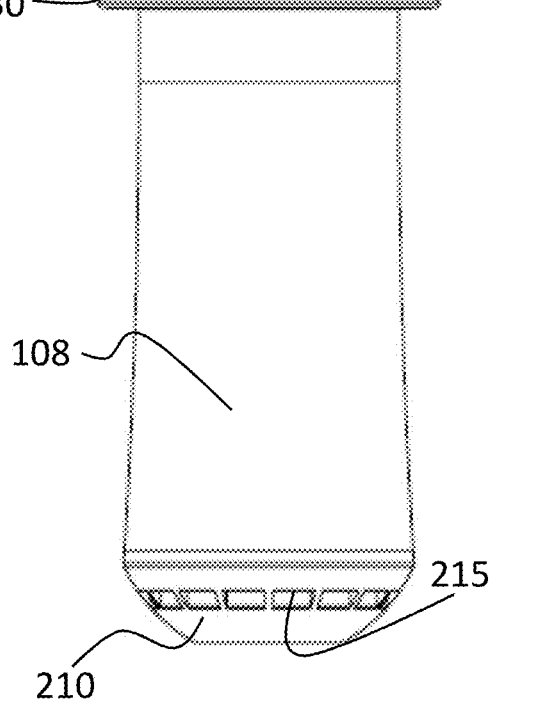
FIG. 9A
FIG. 9B

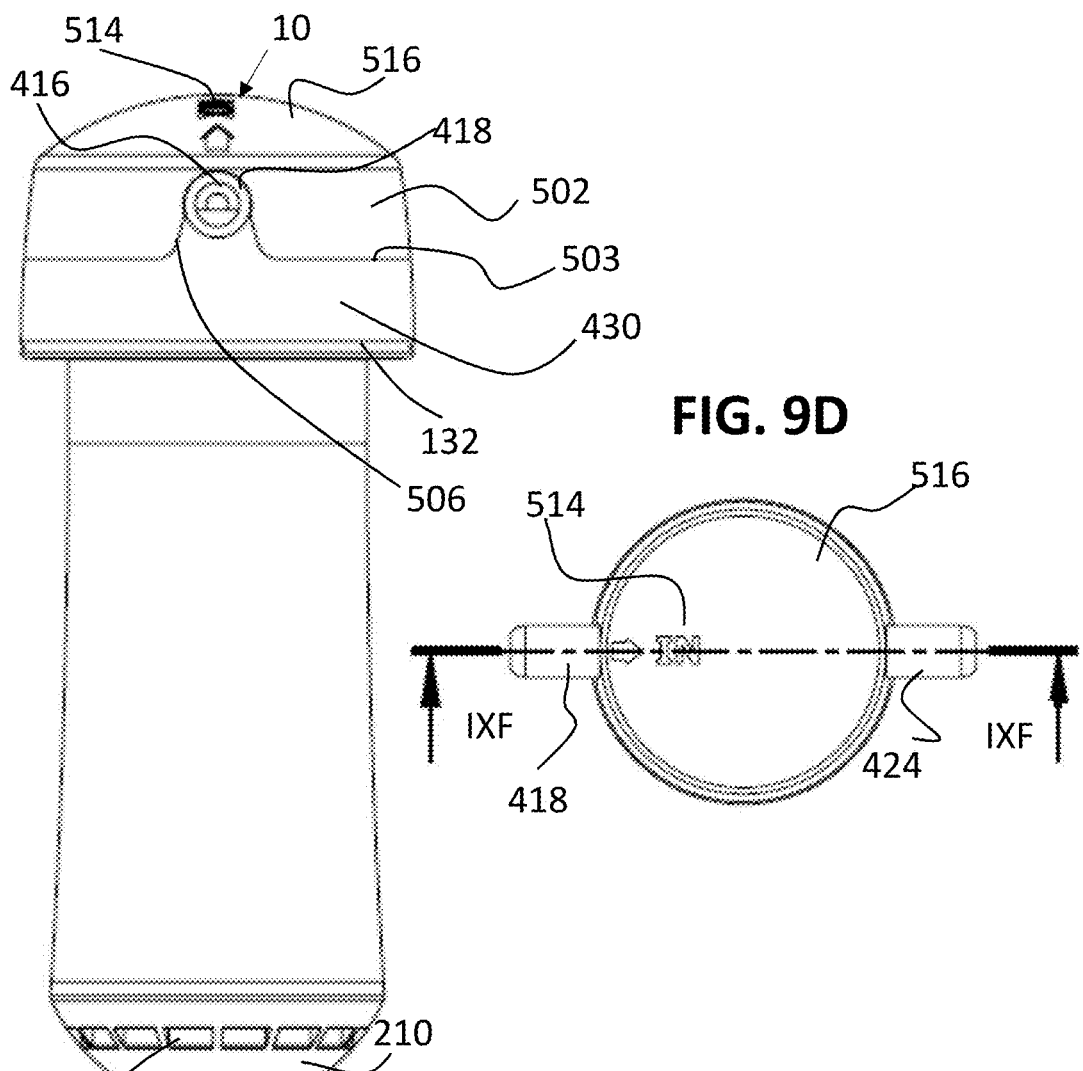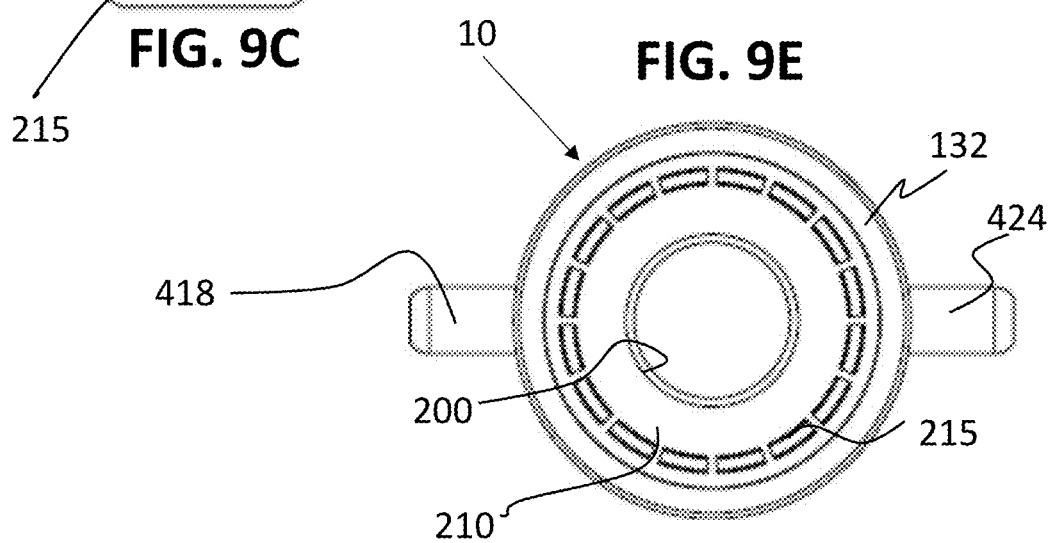

CAPSULE FOR VAPORIZATION OF A LIQUID

RELATED APPLICATION

The present application gains priority from U.S. Provisional Patent Application 62/661,868 filed Apr. 24, 2018 and entitled "A CAPSULE FOR VAPORIZATION OF A LIQUID", which is incorporated herein by reference as if fully set forth herein.

FIELD AND BACKGROUND OF THE INVENTION

The invention, in some embodiments, relates to the field of capsules for vaporization of fluids, and more specifically to capsules for vaporization of a fluid active agent for providing vapor to a subject or to an object, and to systems and methods using such capsules.

The present applicants have disclosed capsules for vaporization of an active agent for treatment of a subject in an airtight space, for example in U.S. patent application Ser. No. 15/438,842, filed on Feb. 22, 2017, which is incorporated herein by reference for all purposes as if fully set forth herein.

However, prior art vaporization capsules suffer from various deficiencies. In some prior art capsules, the user is required to connect one or two covers to the capsule, and to puncture one or two seals. The process of connection and puncturing is prone to human error, particularly when different covers have to be connected at specific locations and/or when there is a significance to the order of the operations. Additionally, in many prior art capsules, the vapor exiting the capsule also includes drops or droplets of the fluid active agent, which may be problematic, for example for safety reasons.

There is thus a need in the art for a vaporization capsule which can be used to vaporize a liquid active agent and to provide vapor thereof, and whose use is less prone to human error and requires fewer steps to be carried out by the user.

SUMMARY OF THE INVENTION

In accordance with embodiments of the present invention, there is provided a vaporization capsule, including:
  an elongate capsule body disposed along a longitudinal axis, including:
    a first wall defining a first volume;
    a second wall disposed about the first wall, and defining a second volume between the second wall and the first wall;
    a third wall portion disposed transversely to the longitudinal axis, the third wall portion disposed within the second wall to define a third volume and engaging the first wall at a first end thereof, the third wall portion including at least one first bore enabling fluid flow from the third volume into the first volume and at least one second bore enabling fluid flow from the second volume into the third volume; and
  a first cover sealingly engaging the elongate capsule body at a first end thereof, the first cover including:
    an exterior perimeter engaging a second end of the first wall;
    an interior wall portion engaging the second wall portion adjacent a second end thereof and including a hollow defined between the exterior perimeter and the interior wall portion; and
    at least one indentation disposed in the interior wall portion, fluidly connecting the first volume and the second volume via the hollow,
  such that a fluid flow path extends from the at least one first bore to the at least one second bore, via the first volume, the at least one indentation, the hollow, and the second volume.

In some embodiments, the vaporization capsule further includes a first substrate disposed within the first volume, the first substrate being adapted to have a liquid active agent absorbed therein or adsorbed thereto.

In some embodiments, the first substrate is further adapted to have a liquid perfuming agent absorbed therein or adsorbed thereto.

In some embodiments, the vaporization capsule further comprising a second substrate disposed within the second volume, the second substrate being adapted to have a liquid perfuming agent absorbed therein or adsorbed thereto. In some embodiments, at least one of the first substrate and the second substrate includes a porous substrate. In some embodiments, at least one of the first substrate and the second substrate includes a sponge. In some embodiments, at least one of the first substrate and the second substrate includes a plurality of porous polymeric particles.

In some embodiments, the vaporization capsule further includes the liquid active agent absorbed in or adsorbed to the first substrate.

In some embodiments, the vaporization capsule further includes the liquid perfuming agent absorbed in or adsorbed to at least one of the first substrate and the second substrate.

In some embodiments, the vaporization capsule further includes a seal adapted to be seated within the third volume, so as to seal the at least one first bore and the at least one second bore and to prevent passage of fluid through the at least one first bore and the at least one second bore.

In some embodiments, the vaporization capsule further includes a second cover adapted to engage the capsule housing at a second end thereof opposite the first end, the second cover including:
  an inlet in fluid communication with the first volume via the at least one first bore; and
  an outlet in fluid communication with the second volume via the at least one second bore,
  such that a fluid flow path exists from the inlet to the outlet.

In some embodiments, the second cover is in threaded engagement with the second end of the capsule housing. In some embodiments, the inlet and the outlet are aligned along a straight line. In other embodiments, the inlet and the outlet are disposed at an angle relative to one another.

In accordance with embodiments of the present invention, there is also provided a method of vaporizing an active agent absorbed in or adsorbed to a substrate disposed within the first volume of the capsule described herein, the method including:
  providing a gas flow into the first volume via the inlet, the gas flow vaporizing at least part of the active agent from the first substrate; and
  receiving a second gas flow including vapor of the active agent from the outlet, via the at least one indentation and the second volume.

In accordance with embodiments of the present invention, there is further provided a method of vaporizing an active agent absorbed in or adsorbed to a first substrate disposed within the first volume of the capsule described herein, the method including:
  removing the seal from the first volume;

connecting a second cover to the capsule housing at a second end thereof opposite the first end, the second cover including:
  an inlet in fluid communication with the first volume via the at least one first bore; and
  an outlet in fluid communication with the second volume via the at least one second bore,
providing a gas flow into the first volume via the inlet, the gas flow vaporizing at least part of the active agent absorbed into or adsorbed onto the first substrate in the first volume; and
receiving a second gas flow including vapor of the active agent from the outlet, via the at least one indentation and the second volume.

In some embodiments, providing a gas flow includes providing a gas flow of at least one of ambient air, pure oxygen, or pure carbon dioxide.

In some embodiments, the active agent includes acetic acid.

In accordance with embodiments of the present invention, there is further provided a system for treatment of an object with an active agent, the system including:
  a vaporization capsule as described herein, the active agent being adsorbed onto or absorbed in the first substrate;
  a gas source, fluidly connected to the inlet of the vaporization capsule, and adapted to provide a gas stream into the first volume of the vaporization capsule via the inlet; and
  an enclosure, fluidly connected to the outlet of the vaporization capsule, and adapted to form an airtight volume around the object,
  wherein active agent vapor, vaporized by the gas stream in the first volume, is adapted to flow through the at least one indentation, the second volume, and the outlet into the airtight volume, thereby to treat the object.

In some embodiments, the enclosure includes a cap, adapted to be placed on a user's head to treat the user's head for lice and nits. In some such embodiments, the active agent includes acetic acid.

In some embodiments, the active agent includes acetic acid. In some embodiments, the gas source is adapted to provide the gas stream as a stream of at least one of ambient air, pure oxygen, or pure carbon dioxide.

In accordance with embodiments of the present invention, there is further provided a method for treating of an object with an active agent, using the vaporization capsule described herein, the method including:
  fluidly connecting a gas source to the inlet of the vaporization capsule;
  fluidly connecting an enclosure to the outlet of the vaporization capsule;
  using the enclosure, forming an airtight volume around the object to be treated; and
  activating the gas source so as to provide a gas stream into the first volume of the vaporization capsule via the inlet, the gas stream causing vaporization of at least part of the active agent in the first volume, and vapor of the active agent exiting the vaporization capsule via the outlet into the enclosure, so as to treat the object.

In some embodiments, the method further includes, prior to fluidly connecting the gas source:
  removing a seal, sealing the at least one first bore and the at least one second bore, from the capsule body; and
  connecting the second cover to the capsule body, such that the inlet is in fluid communication with the at least one first bore and the outlet is in fluid communication with the at least one second bore.

In some embodiments, the enclosure includes a cap, and the forming an airtight volume includes placing the cap on a user's head, so as to treat the user's head for lice and nits. In some such embodiments, the active agent includes acetic acid.

In some embodiments, activating the gas source to provide the gas stream includes activating the gas source to provide a gas stream including at least one of ambient air, pure oxygen, or pure carbon dioxide.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIGS. 2A, 2B, 2C, 2D, and 2E, are, respectively, a perspective view illustration, side, top, and bottom planar view illustrations, and a sectional illustration of a capsule housing forming part of the vaporization capsule of FIGS. 1A and 1B, the sectional illustration taken along section lines IIE-IIE in FIG. 2B;

FIGS. 3A, 3B, 3C, 3D, 3E, and 3F, are, respectively, top and bottom perspective view illustrations, side, top, and bottom planar view illustrations, and a sectional illustration of a bottom cover forming part of the vaporization capsule of FIGS. 1A and 1B, the sectional illustration taken along section lines IIIF-IIIF in FIG. 3D;

FIGS. 4A, 4B, 4C, 4D, 4E, and 4F, are, respectively, top and bottom perspective view illustrations, side, top, and bottom planar view illustrations, and a sectional illustration of a removable seal forming part of the vaporization capsule of FIG. 1A, the sectional illustration taken along section lines IVF-IVF in FIG. 4D;

FIGS. 5A, 5B, 5C, 5D, 5E, 5F, and 5G are, respectively, top and bottom perspective view illustrations, side, top, and bottom planar view illustrations, and two sectional illustrations of a functional upper cover forming part of the vaporization capsule of FIG. 1B, the sectional illustrations taken along respective section lines VF-VF and VG-VG in FIG. 5D;

FIGS. 7A, 7B, 7C, 7D, 7E, and 7F, are, respectively, top and bottom perspective view illustrations, side, top, and bottom planar view illustrations, and a sectional illustration of a working seal forming part of the vaporization capsule of FIG. 1B, the sectional illustration taken along section lines VIIF-VIIF in FIG. 7D;

FIGS. 8A, 8B, 8C, 8D, and 8E are, respectively, a perspective view illustration, side, top, and bottom planar view illustrations, and a sectional illustration of the vaporization capsule of FIG. 1A when constructed, the sectional illustration taken along section lines VIIIE-VIIIE in FIG. 8C;

FIGS. 9A, 9B, 9C, 9D, 9E, and 9F are, respectively, a perspective view illustration, first side, second side, top, and bottom planar view illustration, and a sectional illustration of the vaporization capsule of FIG. 1B when constructed, the sectional illustration taken along section lines IXF-IXF in FIG. 9D;

DESCRIPTION OF SOME EMBODIMENTS OF THE INVENTION

Figure 1A:
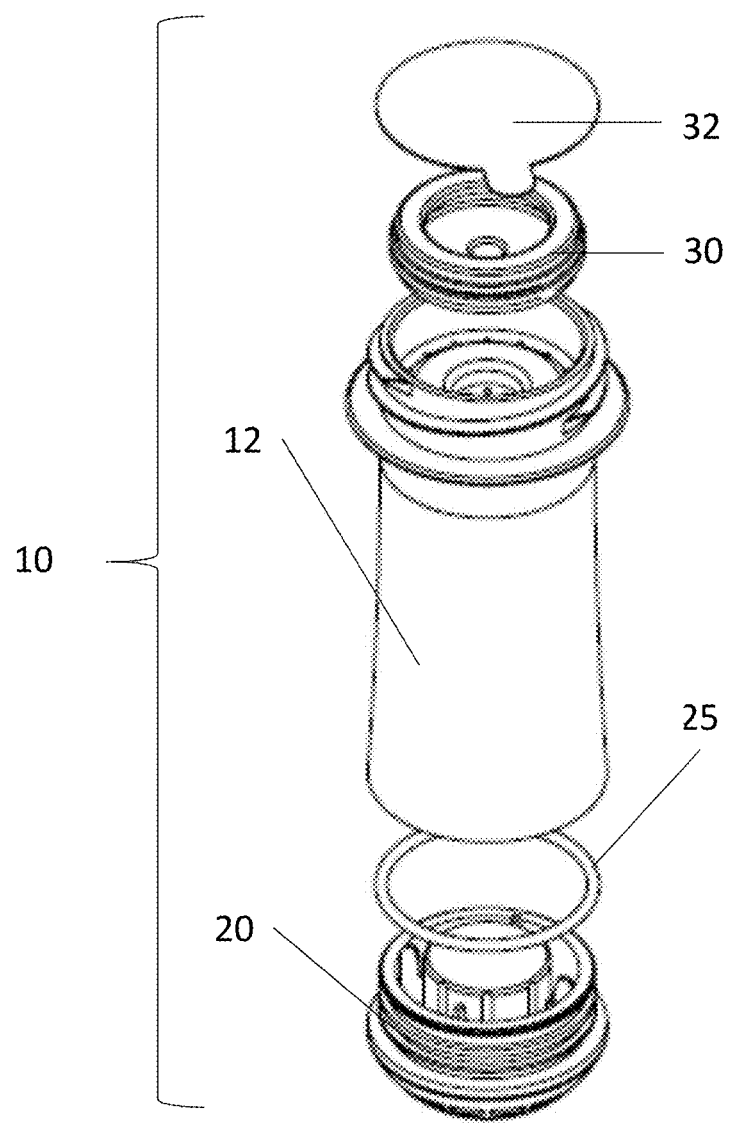
FIGS. 1A and 1B are perspective exploded view illustrations of a vaporization capsule according to an embodiment of the teachings herein in a storage operative orientation and in an operational operative orientation, respectively.

The invention, in some embodiments, relates to the field of capsules for vaporization of fluids, and more specifically to capsules for vaporization of a fluid active agent for providing vapor to a subject or to an object, and to systems and methods using such capsules.

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment of the invention in detail, it is to be understood that the invention is not limited in its applications to the details of construction and the arrangement of the components and/or methods set forth in the following description and/or illustrated in the drawings and/or the Examples. The invention can be implemented with other embodiments and can be practiced or carried out in various ways. It is also understood that the phraseology and terminology employed herein is for descriptive purpose and should not be regarded as limiting.

For purposes of this disclosure, cardinal directions are provided when the longitudinal axis of the capsule is generally perpendicular to the ground or earth and with the inlet and outlet thereof being distal to the ground or earth, as would be the orientation during standard use of the capsule. Thus, an "upper section" is a section which is furthest from the earth when the capsule is in use, a "lower section" is a section which is closer to the earth when the capsule is in use, and so forth. "Inner", "internal", and "inside", as used in this disclosure, refer to a medial direction (toward the middle or center cavity), and conversely "external", "exterior", and "outside" refer to the lateral sides of an element, extending away from the middle or center cavity.

For purposes of this disclosure, curvature directions are provided when the longitudinal axis of the capsule is generally perpendicular to the ground or earth, with the inlet and outlet thereof being distal to the ground or earth, and when the capsule is viewed from above. Thus, a "concave surface" is a surface that, when viewed from above, is concave, and a "convex surface" is a surface that, when viewed from above, is convex. This is true even if the portion seen from above is interior to the capsule.

For the purposes of this disclosure, the terms "unitary construction" and "unitarily formed" relate to an object that is formed of a single piece of material in a single manufacturing process, such as, for example, a piece of plastic that is injection molded to have a specific shape.

Figure 1B:
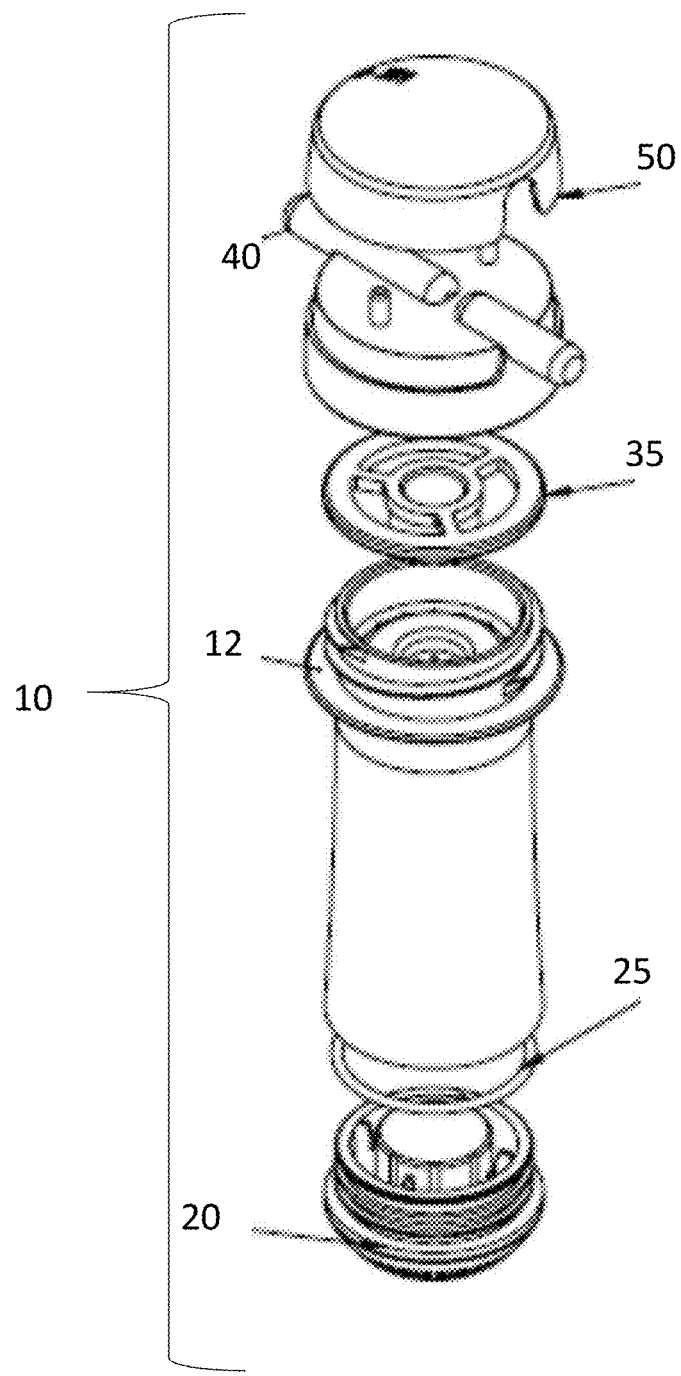

Reference is now made to FIGS. 1A and 1B, which are perspective exploded view illustrations of a vaporization capsule 10 according to an embodiment of the teachings herein, in a storage operative orientation and in an operational operative orientation, respectively.

As seen in FIGS. 1A and 1B, the vaporization capsule 10 includes a capsule body 12, described hereinbelow with respect to FIGS. 2A to 2E, and a bottom cover 20 described hereinbelow with respect to FIGS. 3A to 3F. An elastomeric O-ring 25 is adapted to seal between capsule body 12 and bottom cover 20.

Turning to FIG. 1A, in the storage operative orientation, described in further detail hereinbelow with respect to FIGS. 8A to 8E, a removable seal 30, described hereinbelow with respect to FIGS. 4A to 4F, seals a top end of capsule 10, and is covered by a removable foil 32, such as aluminum foil.

FIG. 1B illustrates the operational operative orientation of capsule 10, described in further detail hereinbelow with respect to FIGS. 9A to 9F, in which the removable seal 30 and the removable foil 32 are removed from the capsule. The removable seal and foil are replaced by a working seal 35, described hereinbelow with respect to FIGS. 7A to 7F, a functional upper cover 40, described hereinbelow with respect to FIGS. 5A to 5F, and a decorative upper cover 50, described hereinbelow with respect to FIGS. 6A to 6F, which form part of capsule 10 in the operational operative orientation.

Figure 2E:
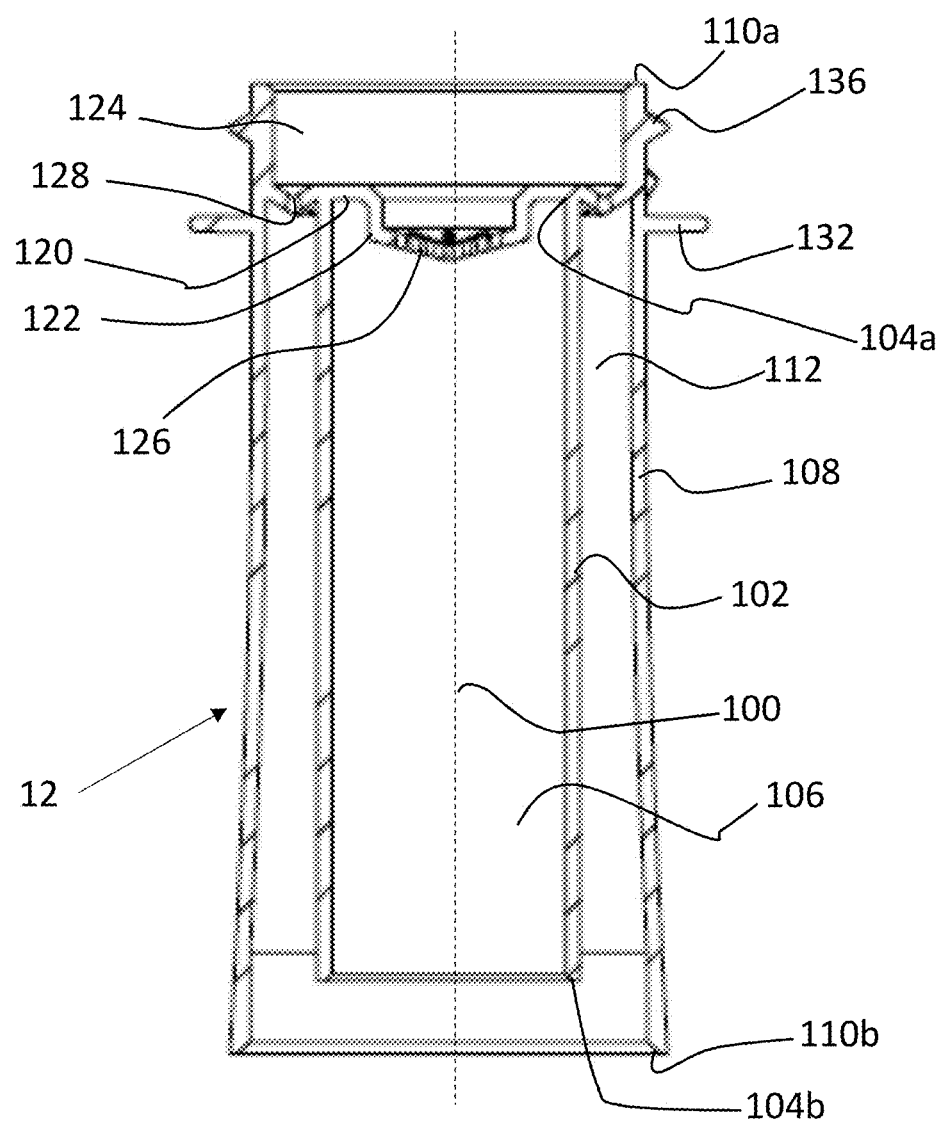

Reference is now made to FIGS. 2A, 2B, 2C, 2D, and 2E, which are, respectively, a perspective view illustration, side, top, and bottom planar view illustrations, and a sectional illustration of capsule body 12 forming part of vaporization capsule 10 of FIGS. 1A and 1B, the sectional illustration taken along section lines IIE-IIE in FIG. 2B.

As seen in FIGS. 2A to 2E, capsule body 12 is generally symmetrical about a longitudinal axis 100 thereof, shown clearly in FIG. 2E. Capsule body 12 includes a first cylindrical wall 102, extending along longitudinal axis 100 and including an upper end 104a and a lower end 104b. A first volume 106 is defined within first cylindrical wall 102. A second generally cylindrical wall 108 extends along longitudinal axis 100 and includes an upper end 110a and a lower end 110b. Second wall 108 surrounds wall 102, thereby defining a second volume 112 between an inner surface of second wall 108 and an outer surface of first wall 102. In some embodiments, first and second cylindrical walls 102 and 108 are concentric.

A third annular wall 120, which may form an annular channel, extends radially inwardly from an inner surface of second wall 108, transversely to longitudinal axis 100. Third annular wall 120 engages upper end 104a of first wall 102. Extending radially from an inner edge of third annular wall 120, and longitudinally into an upper region of first volume 106, is a generally cylindrical seat portion 122, which is adapted, in the storage operative orientation of capsule 10, to receive a portion of seal 30, as described hereinbelow with respect to FIGS. 8A to 8E, and in the operational operative orientation of capsule 10, to receive a portion of working seal 35 and of functional upper cover 40, as described hereinbelow with respect to FIGS. 9A to 9F.

Third annular wall 120 and seat portion 122, together with second wall 108, define an upper volume 124, disposed longitudinally above the third annular wall 120.

A first plurality of throughgoing bores 126 extending through seat portion 122 provide for fluid communication between upper volume 124 and first volume 106. A second plurality of throughgoing bores 128, extending through annular wall 120, provide for fluid communication between upper volume 124 and second volume 112.

It will be appreciated by people of skill in the art that, in some embodiments, the seat portion 122 may be obviated, and annular wall portion 120 may form a generally circular wall portion including the first and second pluralities of bores.

A ridge 132 extend radially outwardly from second wall portion 108, in some embodiments at a position beneath third annular wall 120. As described in further detail hereinbelow with respect to FIGS. 9A-9F, ridge 132 is adapted to engage functional upper cover 40 (FIG. 1B). A male thread 136 is provided on an exterior surface of second wall portion 108, between upper end 110a and ridge 132, the male thread adapted to engage a female thread of functional upper cover 40 (FIG. 1B) as described hereinbelow with respect to FIGS. 9A-9F.

In some embodiments, capsule body 12 may be unitarily formed, for example molded from plastic in a single piece.

Figure 3A:
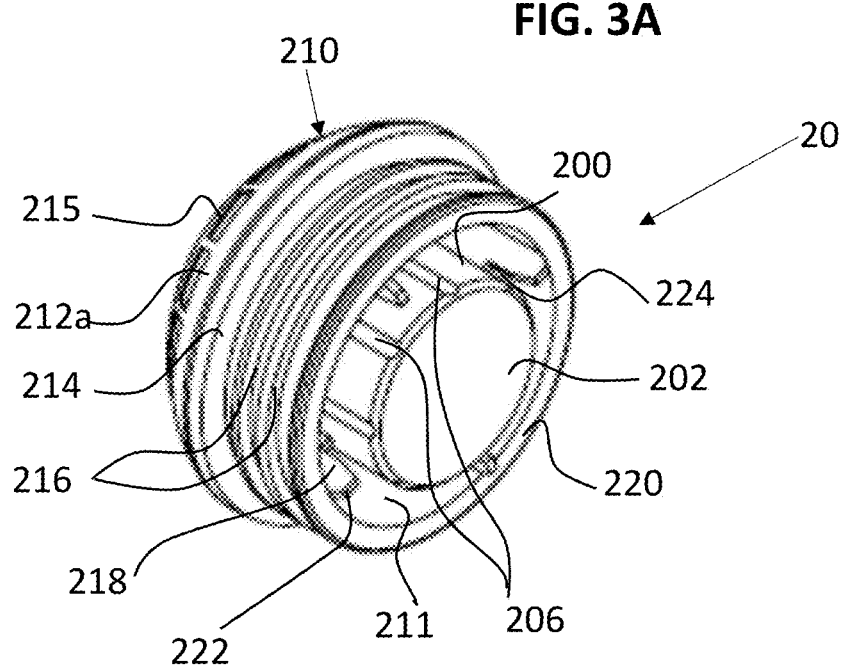
Figure 3B:
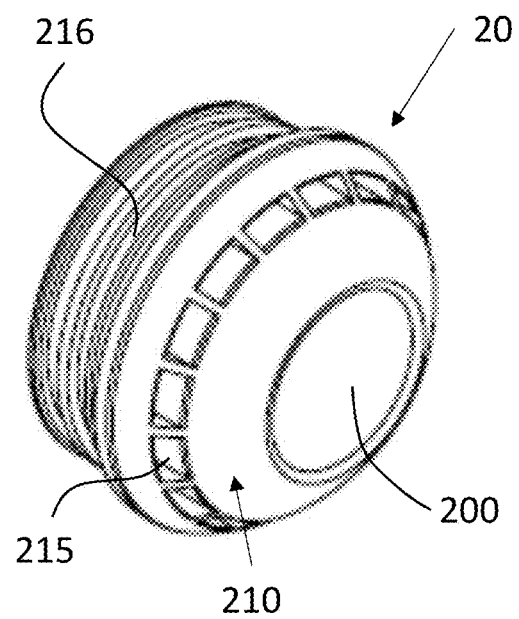
Figure 3E:
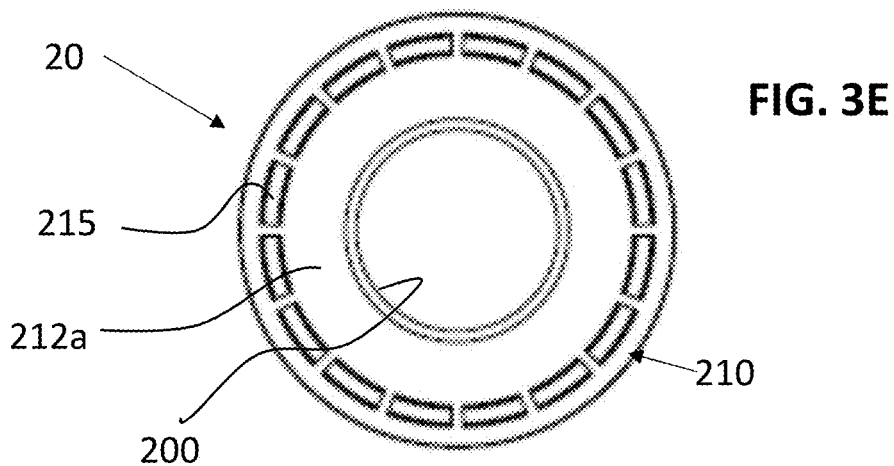
Figure 3F:
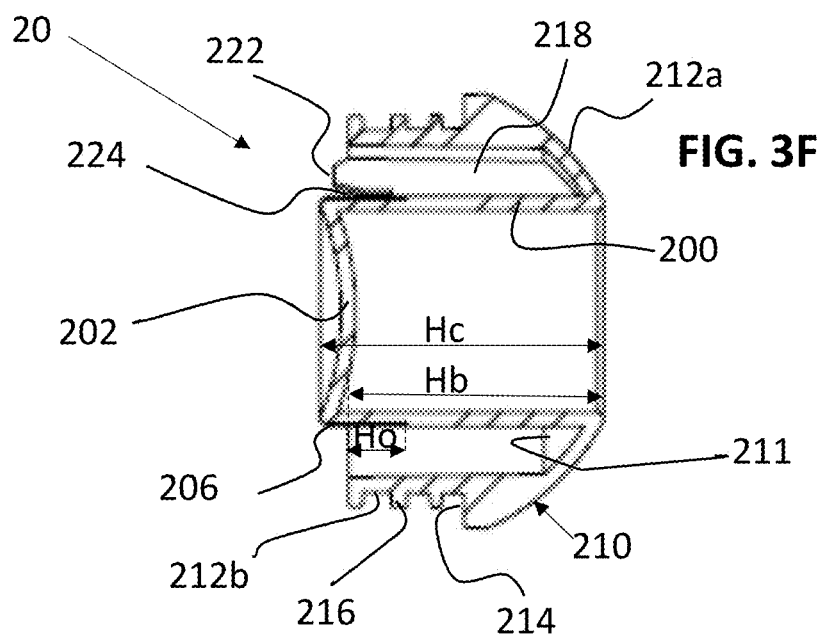

Reference is now made to FIGS. 3A, 3B, 3C, 3D, 3E, and 3F, which are, respectively, top and bottom perspective view illustrations, side, top, and bottom planar view illustrations, and a sectional illustration of bottom cover 20 forming part of vaporization capsule 10 of FIGS. 1A and 1B, the sectional illustration taken along section lines IIIF-IIIF in FIG. 3D.

As seen in FIGS. 3A-3F, bottom cover 20 is side to side symmetrical about a longitudinal axis 204, shown clearly in FIG. 3C. Bottom cover 20 includes a generally cylindrical core 200, terminating at an upper end thereof in a concave wall portion 202. A plurality of slits 206 are distributed about an exterior surface of core 200 adjacent concave wall portion 202. The slits 206 extend only along part of the height of core 200, and do not extend through the entire thickness of core 200, but rather form indentations therein.

A concave base portion 210 extends radially outwardly from a lower end of core 200 about the core. Base portion 210 includes a lower region which is generally concave and forms a cup about core 200. The cup extends into a cylindrical upper region which is concentric with, and disposed about, core 200, and defines a volume 211 between the base portion 210 and the core 200.

An exterior surface of base portion includes a first, generally cupped region 212a, and a second, generally cylindrical region 212b. A outwardly radially extending shoulder 214 connects cupped region 212a and cylindrical region 212b. A plurality of recesses 215 are formed in cupped region 212a. A plurality of ridges 216 extend radially outwardly of cylindrical region 212b. A plurality of radially extending wings 218 connect an inner surface 220 of base portion 210 to an outer surface of core 200, each wing terminating in an upper surface 222 and including a slot 224 at an edge of the wing adjacent core 200, the slot 224 extending only part of the height of the wing 218. In some embodiments, the wings 218 are evenly distributed about the core 200.

It is a particular feature of the present invention that a height Hb of base portion 210 is less than a height Hc of core 200, and there is a height overlap Ho between the slits 206 and the wings 218, such that a portion of the slits 206 is disposed beneath a height of upper surface 222 of wings 218.

In some embodiments, bottom cover 20 is unitarily formed, for example by injection molding of plastic or in any other suitable method.

Figure 3G:
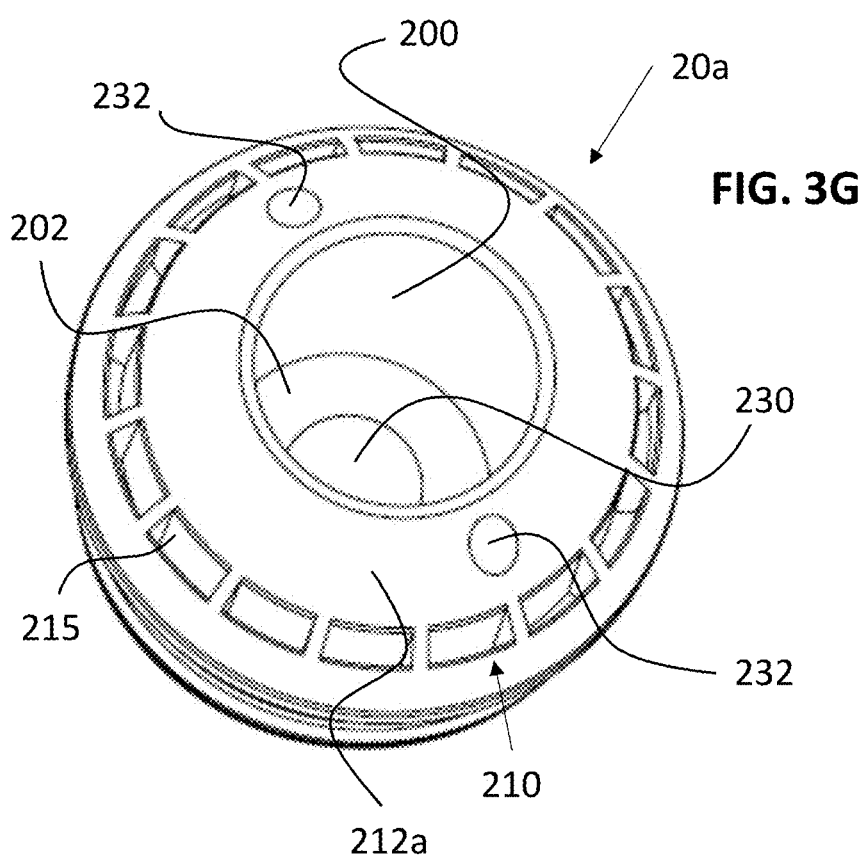
FIG. 3G is a bottom view perspective illustration of another embodiment of the bottom cover of FIGS. 3A to 3F.

Reference is now made to FIG. 3G, which is a bottom view perspective illustration of another embodiment of a bottom cover 20a, similar to bottom cover 20 of FIGS. 3A to 3F. Bottom cover 20a is substantially similar to bottom cover 20, and differs from bottom cover 20 in a few details described herein.

As seen in FIG. 3G, concave wall portion 202 of bottom cover 20a includes an elastomeric portion 230, disposed substantially at a center thereof. Elastomeric portion 230 is adapted to enable injection of an active ingredient, and/or a perfume ingredient, into first volume 106 of capsule body 12, and resealing of the injection opening following such injection, as described in further detail hereinbelow.

In some embodiments, bottom cover 20a includes one or more additional elastomeric portions 232 disposed in cupped region 212a of base portion 210. Elastomeric portion(s) 232 is adapted to enable injection of an active ingredient and/or a perfume ingredient, into second volume 112 of capsule body 12, and resealing of the injection opening, as described in further detail hereinbelow.

In some embodiments, elastomeric portion 230 and/or elastomeric portion(s) 232 are integrally formed with elastomeric O-ring 25 illustrated in FIGS. 1A and 1B.

Figure 4D:
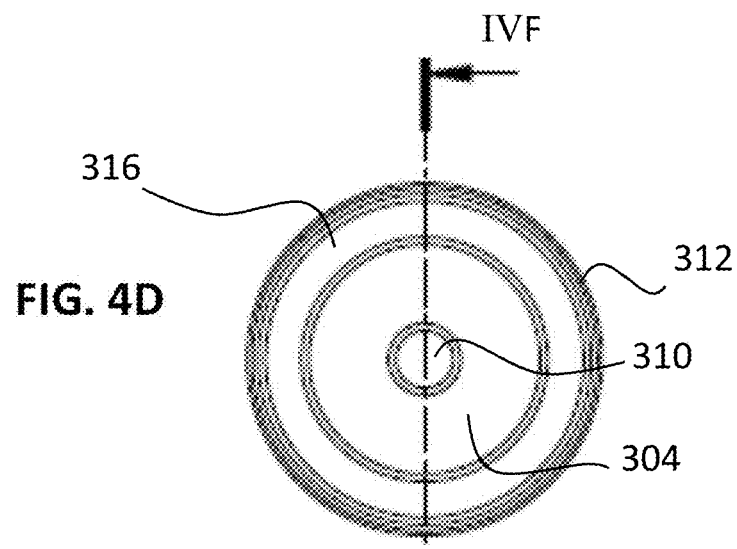
Figure 4E:
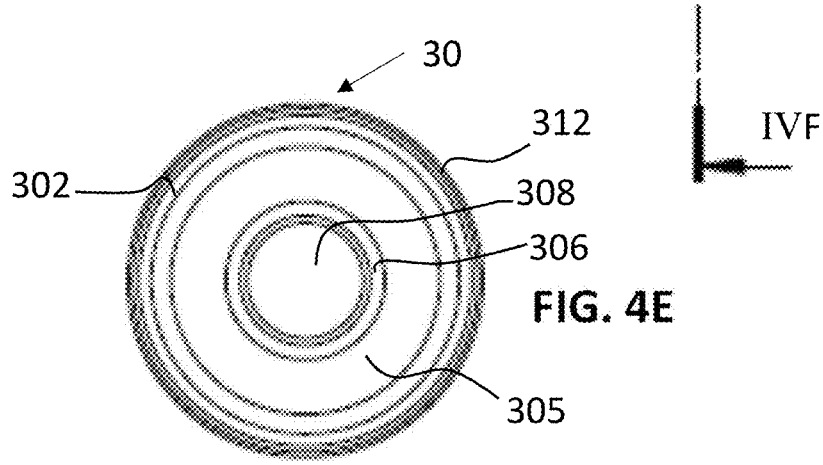

Reference is now made to FIGS. 4A, 4B, 4C, 4D, 4E, and 4F, which are, respectively, top and bottom perspective view illustrations, side, top, and bottom planar view illustrations, and a sectional illustration of removable seal 30 forming part of vaporization capsule 10 of FIG. 1A, the sectional illustration taken along section lines IVF-IVF in FIG. 4D.

Figure 4F:
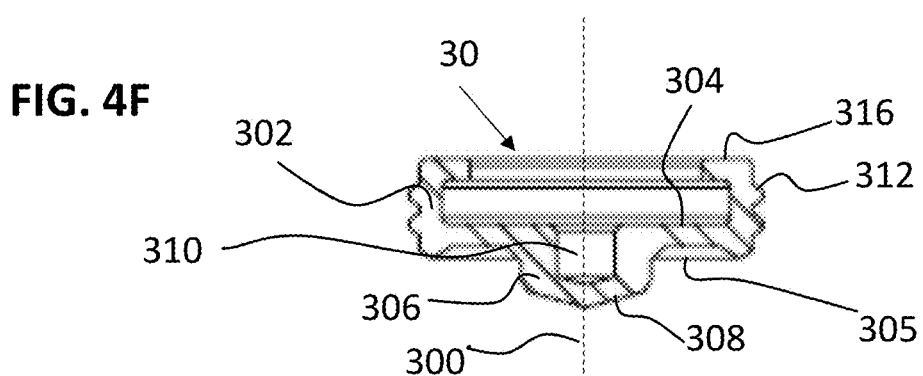

As seen in FIGS. 4A-4F, removable seal 30 is side to side symmetrical about an axis of symmetry 300, shown in FIG. 4F. Seal 30 includes a generally cylindrical seal body 302, terminating at a lower end thereof in a wall portion 304, defining a lower surface 305. Extending longitudinally downwardly from wall portion 304 is a protrusion 306 having a lower surface 308 and defining a hollow 310. The lower surface 308 may be a curved or conical surface. In some embodiments, protrusion 306 may be obviated, such that lower surface 308 may be flush with lower surface 305, as explained in further detail hereinbelow with respect to FIGS. 8A to 8E.

Extending radially outwardly from an exterior surface of seal body 302 are a plurality of ridges 312, adapted for engagement with a seal seat as described in detail hereinbelow with respect to FIGS. 8A to 8F.

Arranged radially inwardly from a top end of seal body 302 is an annular wall portion 316, which forms a lip over the hollow defined by seal body 302 and wall portion 304.

Seal 30 is formed of any material suitable for creating a seal, such as an elastomeric material or a rubber. In some embodiments, seal 30 is unitarily formed, for example by a process of injection molding.

Figure 5D:
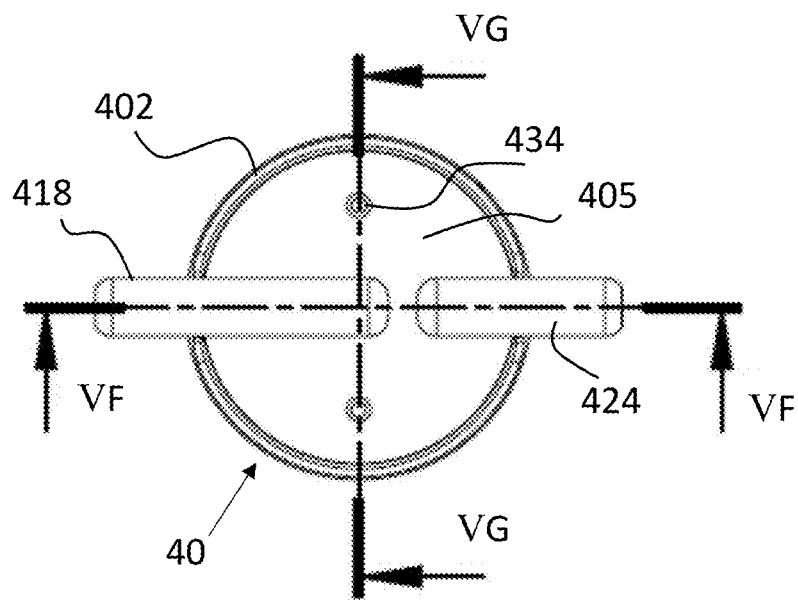
Figure 5E:
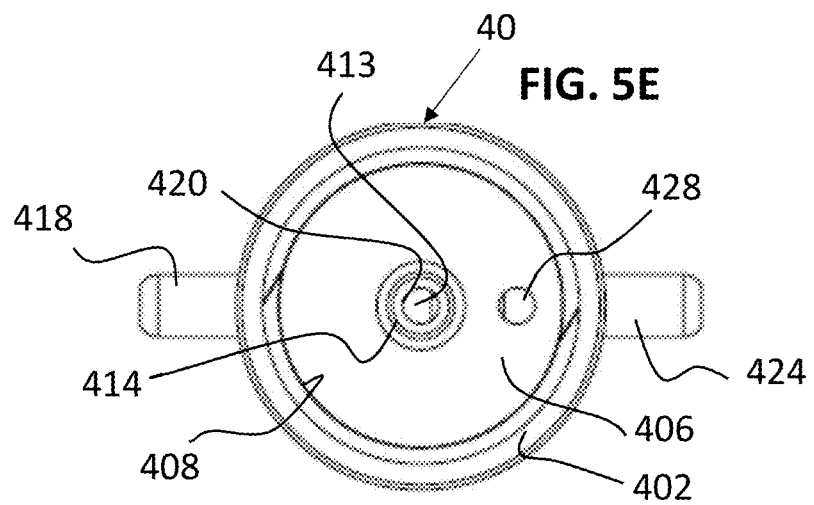
Figure 5F:
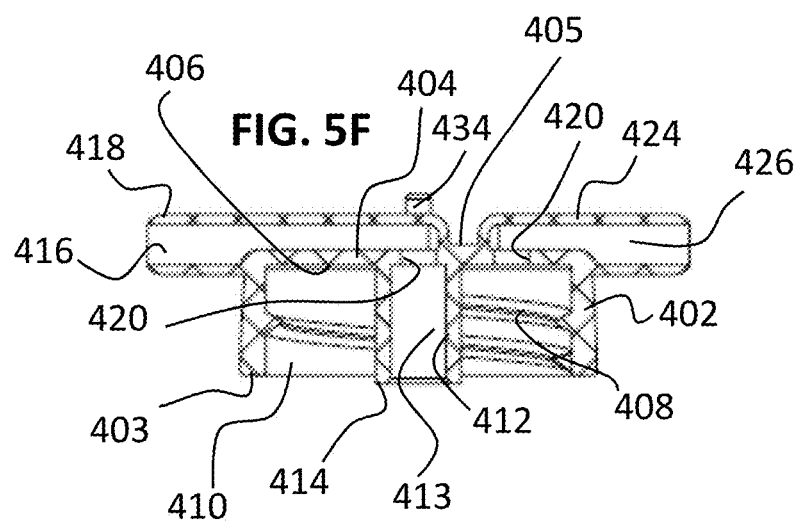
Figure 5G:
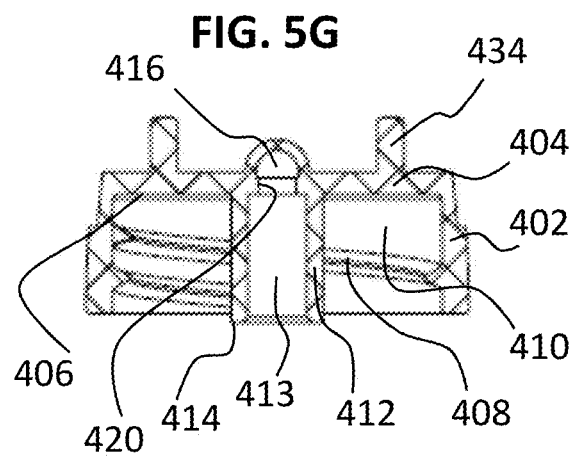

Reference is now made to FIGS. 5A, 5B, 5C, 5D, 5E, 5F, and 5G which are, respectively, top and bottom perspective view illustrations, side, top, and bottom planar view illustrations, and two sectional illustrations of functional upper cover 40 forming part of vaporization capsule 10 of FIG. 1B, the sectional illustrations taken along respective section lines VF-VF and VG-VG in FIG. 5D.

As seen, functional upper cover 40 is side to side symmetrical about an axis of symmetry 400 shown in FIG. 5A, and includes a generally cylindrical body portion 402 having a lower end 403 and terminating at an upper end thereof in a generally circular wall portion 404. Wall portion 404 has an exterior surface 405 and an interior surface 406. A female thread 408 is disposed about an inner surface 410 of body portion 402.

Extending longitudinally downward from wall portion 404, at the center thereof, is a generally tubular portion 412, defining a hollow 413 and terminating at a lower end 414. Tubular portion 412 is in fluid communication with a hollow 416 of a fluid inlet 418, formed on exterior surface 405 of wall portion 404, and extending radially outwardly therefrom, via a throughgoing bore 420 formed at the center of wall portion 404.

A fluid outlet 424, including a hollow 426, is formed on exterior surface 405 of wall portion 404, and extends radially outwardly therefrom. Hollow 426 of outlet 424 is in fluid flow communication with a hollow within cylindrical body portion 402, via a throughgoing bore 428 formed in wall portion 404. In some embodiments, such as that illustrated in FIGS. 5A-5G, outlet 424 is aligned with inlet 418, such that the inlet and outlet form a straight line across a diameter of wall portion 404.

In some embodiments, an outer surface 430 of body portion 402 includes recessed indentations 432 along part of the circumference and part of the height thereof. In some embodiments, a pair of pins 434 extend longitudinally upwardly from exterior surface 405 of wall portion 404. Indentations 432 together with pins 434 are adapted for engagement and alignment of decorative upper cover 50, as described hereinbelow with respect to FIGS. 9A to 9F.

In some embodiments, functional upper cover 40 may be unitarily formed, such as by injection molding of a single piece of plastic, or using any other suitable process.

Figure 6A:
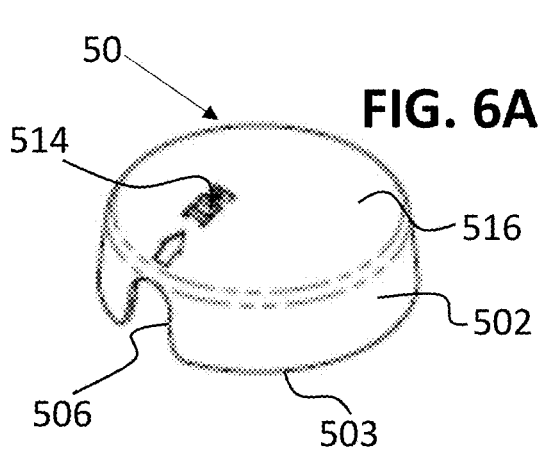
FIGS. 6A, 6B, 6C, 6D, 6E, and 6F, are, respectively, top and bottom perspective view illustrations, side, top, and bottom planar view illustrations, and a sectional illustration of a decorative upper cover forming part of the vaporization capsule of FIG. 1B, the sectional illustration taken along section lines VIF-VIF in FIG. 6D.
Figure 6B:
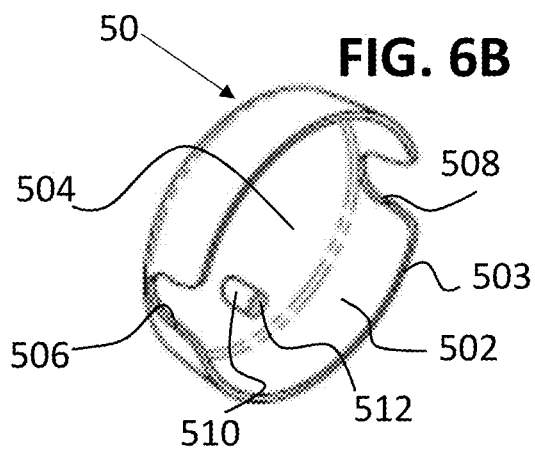
Figure 6C:
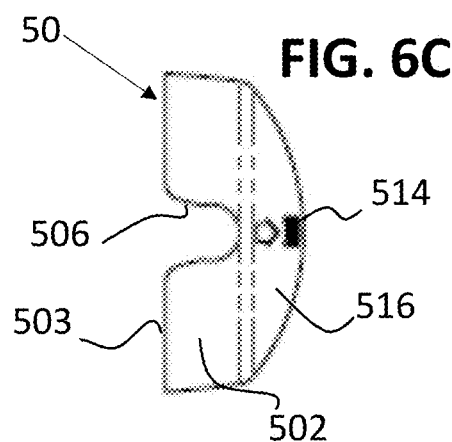
Figure 6D:
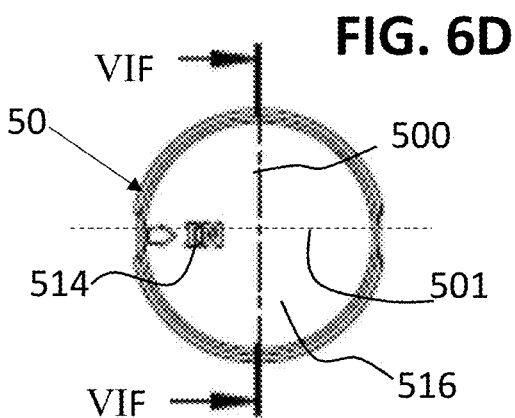
Figure 6E:
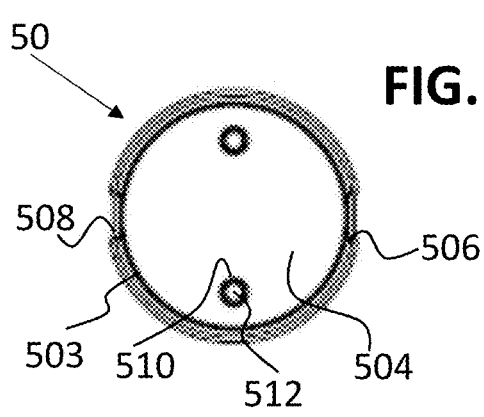
Figure 6F:
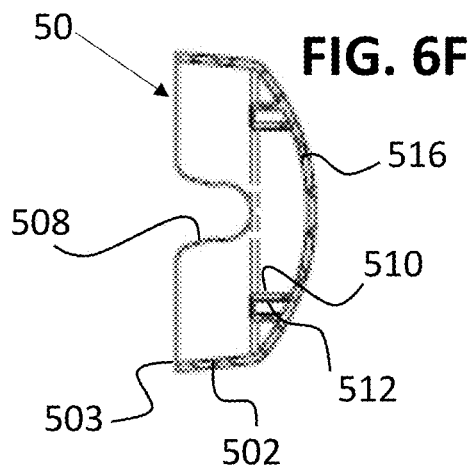

Reference is now made to FIGS. 6A, 6B, 6C, 6D, 6E, and 6F, which are, respectively, top and bottom perspective view illustrations, side, top, and bottom planar view illustrations, and a sectional illustration of decorative upper cover 50 forming part of vaporization capsule 10 of FIG. 1B, the sectional illustration taken along section lines VIF-VIF in FIG. 6D.

As seen, decorative upper cover 50 is substantially side to side symmetrical about first and second axes of symmetry 500 and 501 shown in FIG. 6D, other than graphic indications on the exterior thereof. Decorative upper cover 50 includes a generally cylindrical body portion 502 terminating at a lower side thereof in an end 503 and at an upper side thereof in a convex wall 504. A pair of slots 506 and 508 are cut out of cylindrical body 502, and are adapted to accommodate the inlet and outlet of the functional upper cover 40, as explained in further detail hereinbelow with respect to FIGS. 9A to 9F. As such, in the illustrated embodiment the slots 506 and 508 are aligned along a single diameter of decorative upper cover 50. However, it is appreciated that the slots may be disposed at any location about cylindrical body portion 502 suitable for alignment with the inlet and outlet of the functional upper cover 40.

Extending longitudinally downward from convex wall 504 are a pair of tubular protrusions 510, each defining a bore 512. Bores 512 are adapted to receive pins 434 of functional upper cover 40 (FIG. 5A) as described in further detail hereinbelow with respect to FIGS. 9A to 9F.

In some embodiments, a graphical indication 514 is disposed on an outer surface 516 of convex wall 504, in alignment with slot 506, so as to indicate the location of the inlet of functional upper cover 40. It is appreciated that in some embodiments the graphical indication 514 may be obviated, and in some embodiments a second, or alternate, graphical indication (not shown) may be provided on outer surface 516 in alignment with slot 508, so as to indicate the location of the outlet. The graphical indication(s) 514 is designed to assist the user in connecting the capsule 10 to the system in which the capsule is used, as described hereinbelow with respect to FIGS. 10 and 11.

Figure 7A:
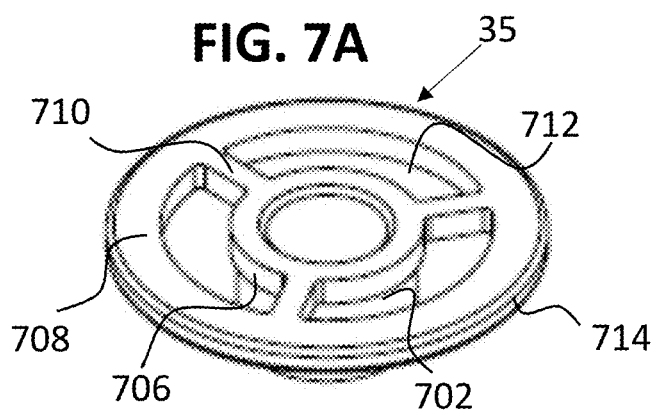
Figure 7B:
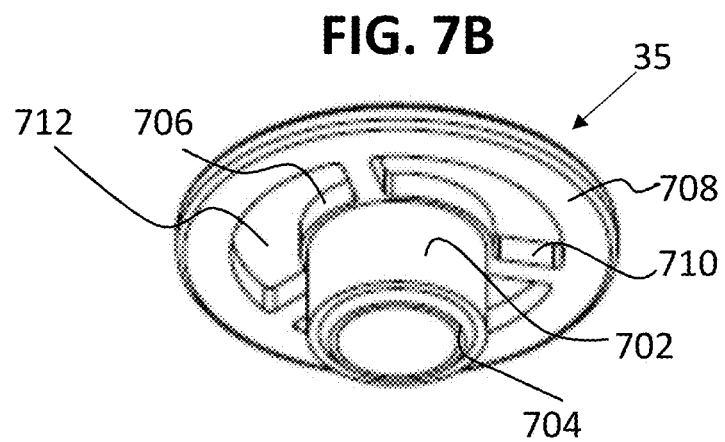
Figure 7C:
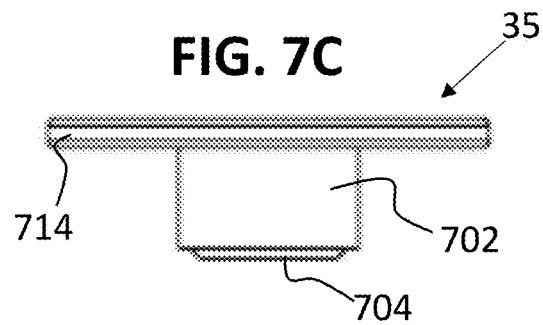
Figure 8C:
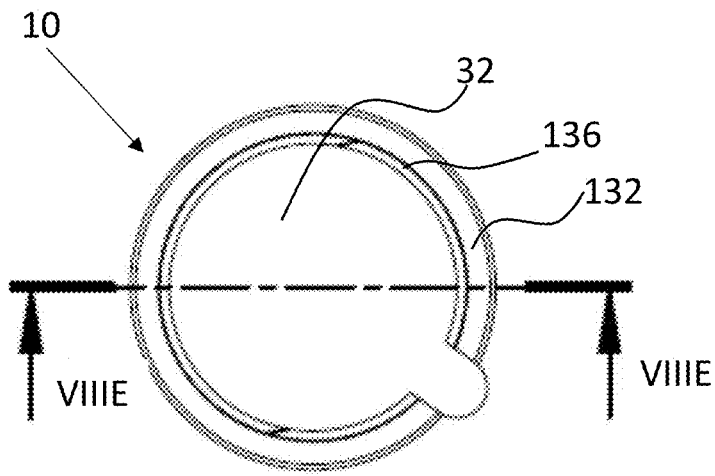
Figure 8D:
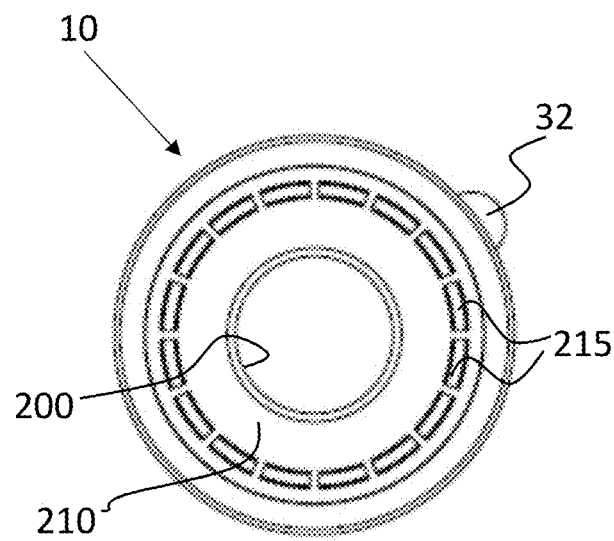
Figure 8E:
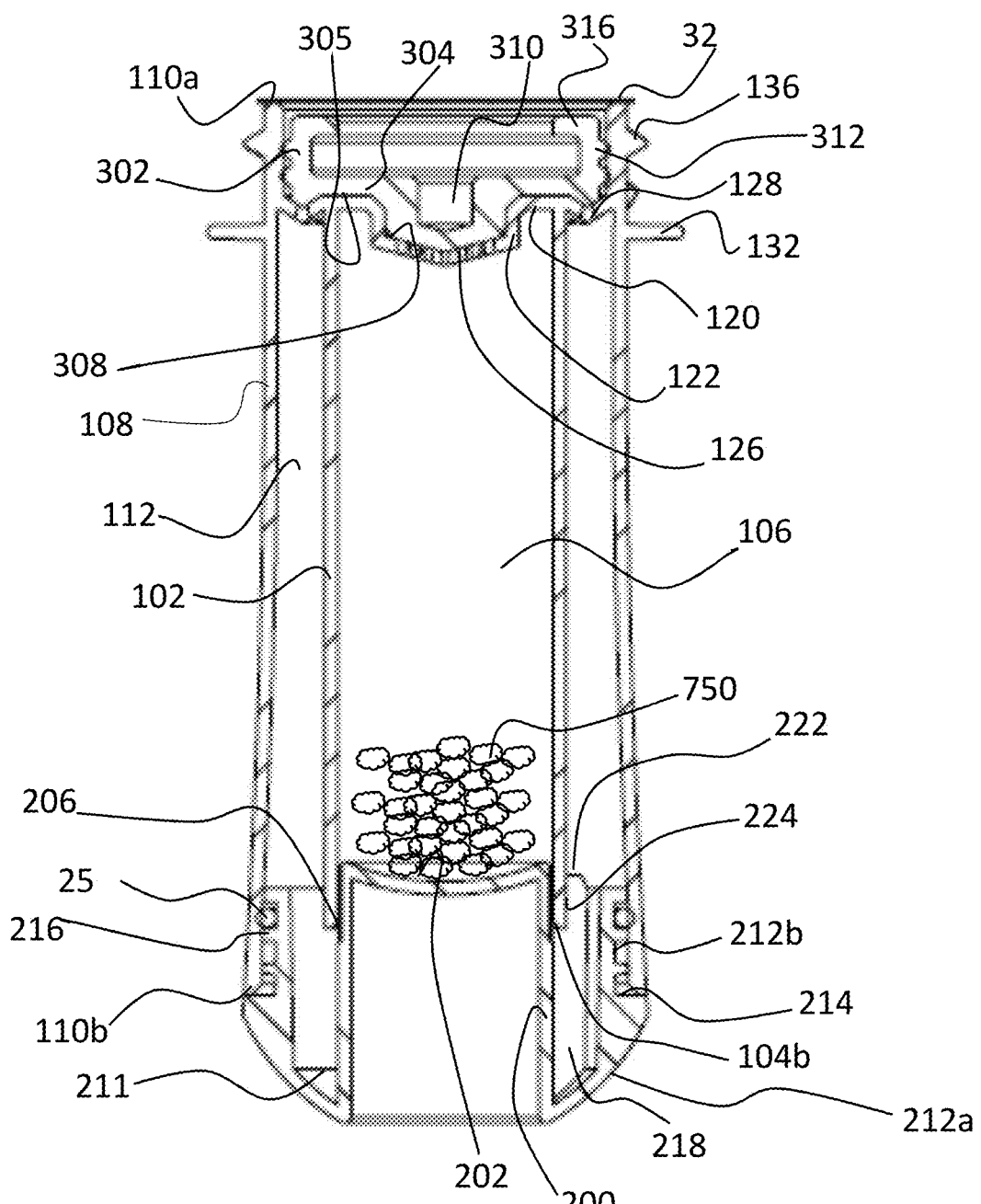
Figure 9F:
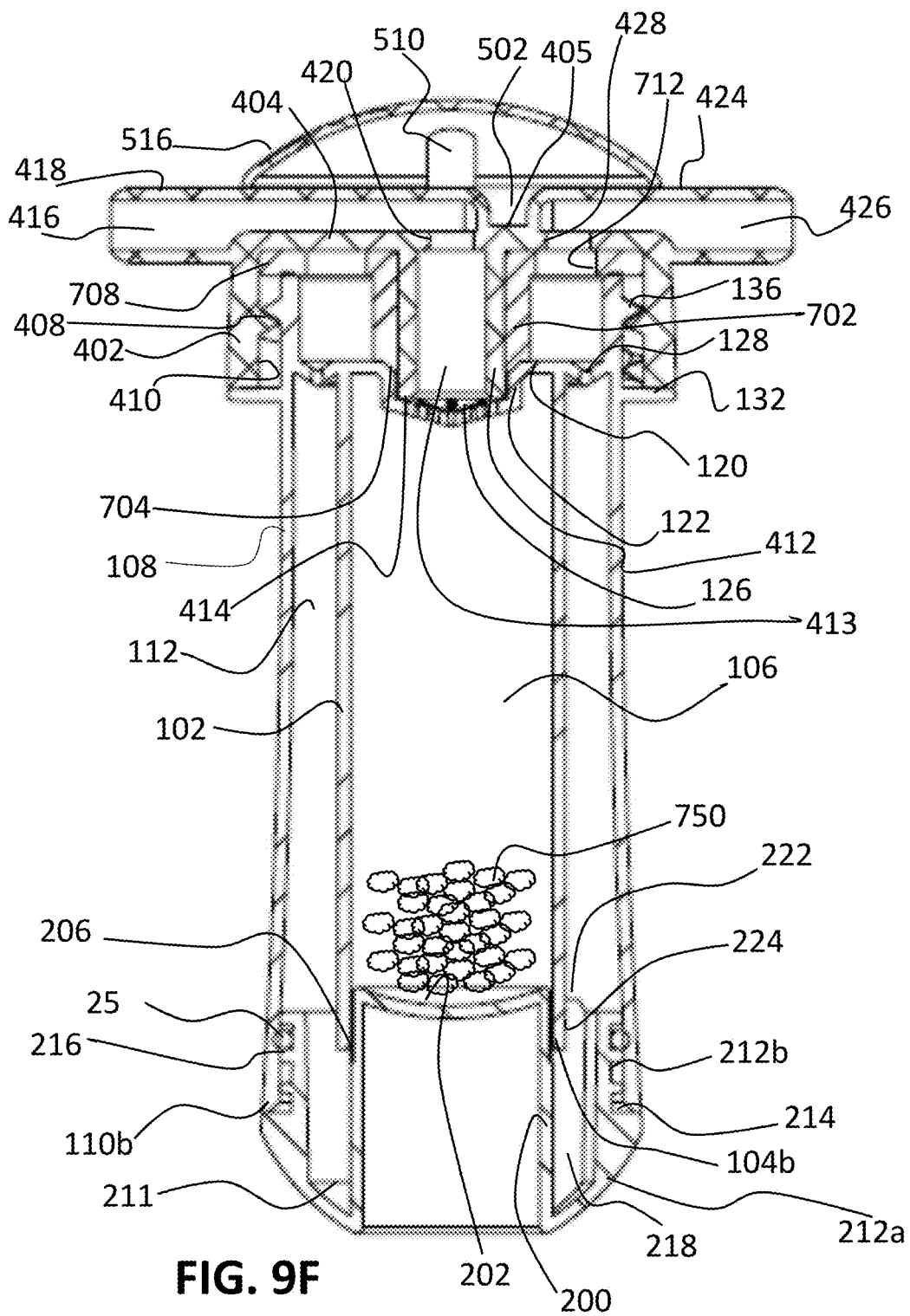

Reference is now made to FIGS. 7A, 7B, 7C, 7D, 7E, and 7F, which are, respectively, top and bottom perspective view illustrations, side, top, and bottom planar view illustrations, and a sectional illustration of working seal 35 forming part of the vaporization capsule of FIG. 1B, the sectional illustration taken along section lines VIIF-VIIF in FIG. 7D.

As seen in FIGS. 7A-7F, working seal 35 includes a generally cylindrical seal core 702, terminating at a lower end thereof in a sealing ring 704, and having an upper ridge 706. Disposed about upper ridge 706 is an annular portion 708, connected to upper ridge 706 by a plurality of connecting bars 710, here illustrated as three connecting bars. Hollows 712, which allow fluid flow therethrough, are defined between ridge 706, annular portion 708, and bars 710. In some embodiments, a sealing ring 714 is disposed on a radial outward edge of annular portion 708.

As described hereinbelow with respect to FIGS. 9A to 9F, sealing ring 704 and sealing ring 714 are adapted to seal between housing 12 and functional upper cover 40, when capsule 10 is in the operational operative orientation.

Reference is now made to FIGS. 8A, 8B, 8C, 8D, and 8E, which are, respectively, a perspective view illustration, side, top, and bottom planar view illustrations, and a sectional illustration of vaporization capsule 10 of FIG. 1A when constructed, and in the storage operative orientation. The sectional illustration is taken along section lines VIIIE-VIIIE in FIG. 8C.

As seen in FIGS. 8A-8E, in the storage orientation of capsule 10, bottom cover 20 is connected to a bottom end of the capsule body 12, with elastomeric O-ring 25 disposed therebetween. Seal 30 seals a top end of the capsule body 12, and is covered by sealing foil 32.

More specifically, cylindrical portion 212b of bottom cover 20 is disposed within second cylindrical wall 108 of capsule body 12, such that ridges 216 of bottom cover 20 engage an inner surface of second wall portion 108, and such that lower end 110b of the capsule body engages shoulder 214 of the bottom cover 20. Thus, bottom cover 20 becomes lodged in place relative to capsule body 12. Elastomeric O-ring 25 is illustrated as being seated between two of ridges 216 and the inner surface of second wall portion 108.

An outer surface of core 200 of bottom cover 20 engages an inner surface of first cylindrical wall 102 of capsule body 12, such that lower end 104b of first wall 102 is seated within slots 224 of wings 218, beneath upper surfaces 222 thereof.

Because of the height overlap Ho (FIG. 3F) between slits 206 and wings 218, and because slits 206 are carved into the material of core 200 of bottom cover 20, a fluid flow path exists between first volume 106 and second volume 112 of capsule body 12, via slits 206 and volume 211 of bottom cover 20. It will be appreciated that, in some embodiments, slits 206 are sized and configured such that the flow path between first volume 106 and second volume 112 will only be suitable for passage of gas, and not for passage of liquid droplets.

It will further be appreciated that the engagement between bottom cover 20 and capsule body 12 is air tight and water tight, such that fluid flowing through the flow path between the first volume 106 and the second volume 112 cannot "escape" via the connection between the capsule body and the bottom cover.

In the storage operative orientation, illustrated in FIGS. 8A-8E, removable seal 30 is seated within volume 124 of capsule housing 12. In this arrangement, ridges 312 of seal 30 engage the inner surface of the second cylindrical wall 108, and wall 316 of removable seal 30 is disposed beneath upper end 110a of capsule housing 12.

When seal 30 is seated within volume 124, wall portion 304 of seal 30 engages annular wall portion 120 of capsule housing 12, such that lower surface 305 seals second plurality of bores 128, and protrusion 306 is seated within seat portion 122 of capsule housing 12, such that lower surface 308 seals bores 126.

As discussed hereinabove with reference to FIGS. 2A-2E, in some embodiments, seat 122 may be obviated, and wall 120 may be a circular wall including bores 126 and 128. In such embodiments, protrusion 306 would also be obviated, and wall portion 304 would be a circular wall portion, such that lower surface 305 thereof would engage and seal bores 126 as well as bores 128.

In some embodiments which include bottom cover 20 of FIGS. 3A to 3F, prior to connection of bottom cover 20 to capsule housing 12 and sealing thereof, a first substrate 750 is inserted into first volume 106, the first substrate having an active agent in a liquid state absorbed therein or adsorbed thereto. In some embodiments, the first substrate may also have a perfuming agent in a liquid state absorbed therein or adsorbed thereto.

In some embodiments which include bottom cover 20 of FIGS. 3A to 3F, prior to connection of bottom cover 20 to capsule housing 12 and sealing thereof, a second substrate is inserted into second volume 112, the second substrate having the perfuming agent in a liquid state absorbed therein or adsorbed thereto.

In some embodiments which include bottom cover 20a of FIG. 3G, prior to connection of bottom cover 20a to capsule housing 12 and sealing thereof, a first substrate 750 is inserted into first volume 106. Following connection of bottom cover 20a to capsule housing 12, an active agent in a liquid state is injected into the first volume 106 via elastomeric portion 230, such that the active agent is absorbed in or adsorbed to first substrate 750. In some embodiments, a perfuming agent in a liquid state is also injected into the first volume 106 via elastomeric portion 230, and is absorbed in or adsorbed to first substrate 750.

In some embodiments which include bottom cover 20a of FIG. 3G, prior to connection of bottom cover 20 to capsule housing 12 and sealing thereof, a second substrate is inserted into second volume 112. Following connection of bottom cover 20a to capsule housing 12, a perfuming agent in a liquid state is injected into the second volume 112 via elastomeric portion(s) 232, such that the perfuming agent is absorbed in or adsorbed to the second substrate.

In some embodiments, the perfuming agent may be an oil or another hydrophobic perfuming agent.

In some embodiments, the first substrate 750 and/or the second substrate includes, or is, one or more porous particles. For example, the first substrate and/or the second substrate may be formed as a single lump, several smaller lumps, or a large number of unbound small crumb-size pieces, spherical or of another shape, including amorphous pieces. The porous particle(s) may be amorphous or of a defined spatial shape, such as a cylinder, a sphere, etc., and may be composed of materials such as thermoplastic polymers, glass, sponge, etc, for example as described in in U.S. patent application Ser. No. 15/438,842, which is incorporated by reference for all purposes as if fully set forth herein.

In some embodiments, the first substrate and second substrate may be of the same type, structure, and/or dimensions. In other embodiments, the first and second substrate are of different types, and/or have a different structure or different dimensions.

It will be appreciated that the first substrate 750 and/or the second substrate, and particles thereof, are designed to improve, and control timing of, vaporization of the active agent and/or the perfuming agent absorbed therein or adsorbed thereto, as explained in further detail hereinbelow with respect to FIG. 10.

Reference is now made to FIGS. 9A, 9B, 9C, 9D, 9E, and 9F, which are, respectively, a perspective view illustration, first side, second side, top, and bottom planar view illustration, and a sectional illustration of vaporization capsule 10 of FIG. 1B when constructed and in an operational operative orientation. The sectional illustration is taken along section lines IXF-IXF in FIG. 9D.

In the operational operative orientation illustrated in FIGS. 9A-9F, there is no change in the connection between bottom cover 20 and capsule body 12 relative to the description provided hereinabove with respect to FIGS. 8A to 8E. However, in the operational operative orientation, the seal 30 (illustrated in FIGS. 8A-8E) is removed from the capsule body 12, and working seal 35, functional upper cover 40, and decorative upper cover 50 are attached to the upper end of capsule body 12.

As seen in FIGS. 9A to 9F, volume 124 is free of seal 30. Cylindrical body portion 402 of functional upper cover 40 is disposed about an upper portion of second cylindrical wall 108 of capsule housing 12, by threaded engagement of male threads 136 with female threads 408. Lower end 403 of body portion 402 of functional upper cover 40 engages ridge 132, such that the connection therebetween is sealed for passage, or "escape", of fluid therethrough.

In this orientation, lower end 414 of tubular portion 412 of functional upper cover 40 is seated within seat portion 122, such that hollow 413 of tubular portion 412, and hollow 416 of inlet 418, are in fluid communication with first volume 106 via bores 126. Similarly, second volume 112 is in fluid communication with hollow 426 of outlet 424 of functional upper cover 40, via bores 128 and volume 126 of capsule housing 12. As such, a single flow path is defined from inlet 418 and hollow 416 thereof, to outlet 424 and hollow 426 thereof, via bore 420, hollow 413 of tubular portion 412, bores 126 of seat portion 122, first chamber 106, slits 206, hollow 211, second chamber 112, bores 128 of annular wall portion 120, chamber 124, and bore 428.

As discussed hereinabove with reference to FIGS. 2A-2E, in some embodiments, seat 122 may be obviated, and wall 120 may be a circular wall including bores 126 and 128. In such embodiments, tubular portion 412 would be suitable sized so as to surround and bores 126 and define a flow path from the inlet into the first chamber.

Working seal 35 is disposed between functional upper cover 40 and capsule housing 12. Specifically, cylindrical core 702 of working seal 35 is disposed about tubular portion 412 of functional upper cover 40, and sealing ring 704 engages a surface of annular wall 120 surrounding seat 122. A lower surface of annular ring 708 of working seal 35 engages upper end 110a of capsule housing 12, and sealing ring 714 of working seal 35 seals against an inner surface of cylindrical body portion 402 of functional upper cover 40. Hollows 712 of working seal 35 enable fluid flow from bores 128 to outlet 424.

Decorative upper cover 50 is disposed over functional upper cover 40, such that inlet 418 is disposed within slot 506, outlet 424 is disposed within slot 508, and graphical indication 514 indicates inlet 418. Decorative upper cover 50 is kept in position relative to functional upper cover 40 by engagement of pins 434 within bores 512, and by engagement of cylindrical body portion 502 of decorative cover 50 within recesses 432 of outer surface 430 of body portion 402 of functional cover 40.

In use, a stream of gas is provided into hollow 416 of inlet 418, and flows from there in to first volume 106, where it vaporizes the active agent (and in some embodiments perfuming agent) adsorbed to or absorbed by first substrate 750. The active agent vapor, together with the stream of gas, flows through slits 206 and hollow 211 into second volume 112, where, in some embodiments, the gas flow vaporizes the perfuming agent from the second substrate. From second volume 112, the gas flow, including the active agent vapor and in some embodiments also vapor of the perfuming agent, passes via bores 128, volume 124, and bore 428, out of outlet 424. In some embodiments, no liquid droplets of the active agent and/or of the perfuming agent are emitted from outlet 424.

Specific uses and applications of the capsule of FIGS. 1A to 9F are described hereinbelow with reference to FIGS. 10 and 11.

Figure 10:
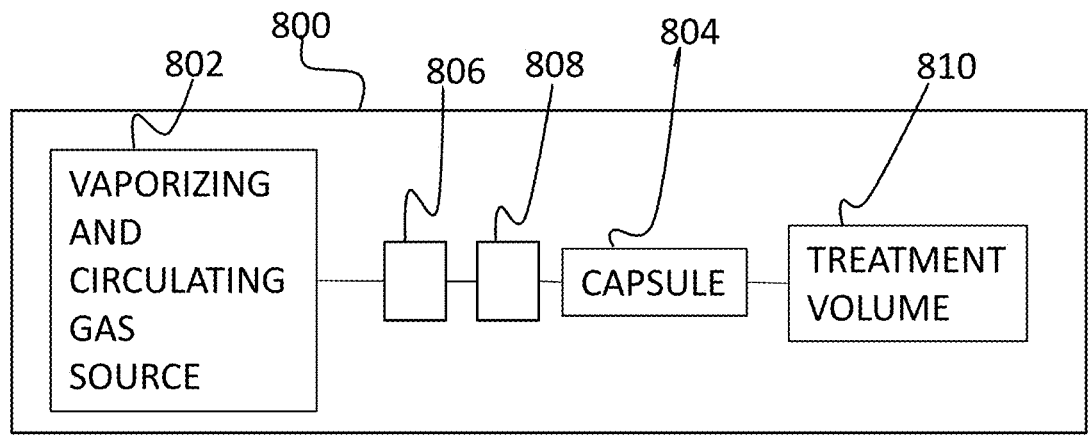
FIG. 10 is a schematic block diagram of an embodiment of a system for treating an object with gas or vapor using the capsule of FIGS. 1A to 9F according to an embodiment of the teachings herein.

Reference is now made to FIG. 10, which is a schematic block diagram of an embodiment of a system 800 for treating an object with gas or vapor using vaporization capsule 10 of FIGS. 1A to 9F, according to an embodiment of the teachings herein.

System 800 includes a vaporizing and circulating gas source 802 adapted to provide a vaporizing and circulating gas, either from the ambient environment of the system or from a dedicated vaporizing and circulating gas storage (not shown). The vaporizing and circulating gas source 802 is fluidly attached to the inlet (e.g. inlet 418) of a capsule 804, similar to capsule 10 of FIGS. 1A to 9F.

In some embodiments, the gas source 802 is attached to capsule 804 via a suitable tube 806 and a suitable adapter 808. In other embodiments, no tubes or adapters are required, for example when the capsule 804 is housed within the housing of gas source 802.

An outlet (e.g. outlet 424) of capsule 804 is fluidly attached to an airtight treatment volume 810. Volume 810 may be, for example, a cap to be placed on a subject's head for the treatment of lice and nits, or an airtight wrapper placed around an object for the treatment of vermin. In some embodiments, the capsule may be directly connected to the treatment volume, possibly via a second adapter similar to adapter 808 described above. In other embodiments, fluid communication between capsule 804 and volume 810 may be via a connecting tube.

It will be appreciated by people skilled in the art that the fluid communications between gas source 802 and capsule 804, and between capsule 804 and volume 810, may be achieved using any suitable means. As such, these connections may be indirect, and may include one or more connecting tubes. Alternately, these connections may be direct, requiring no connecting tubes, depending on the structure suitable for each specific application and active agent.

Figure 11:
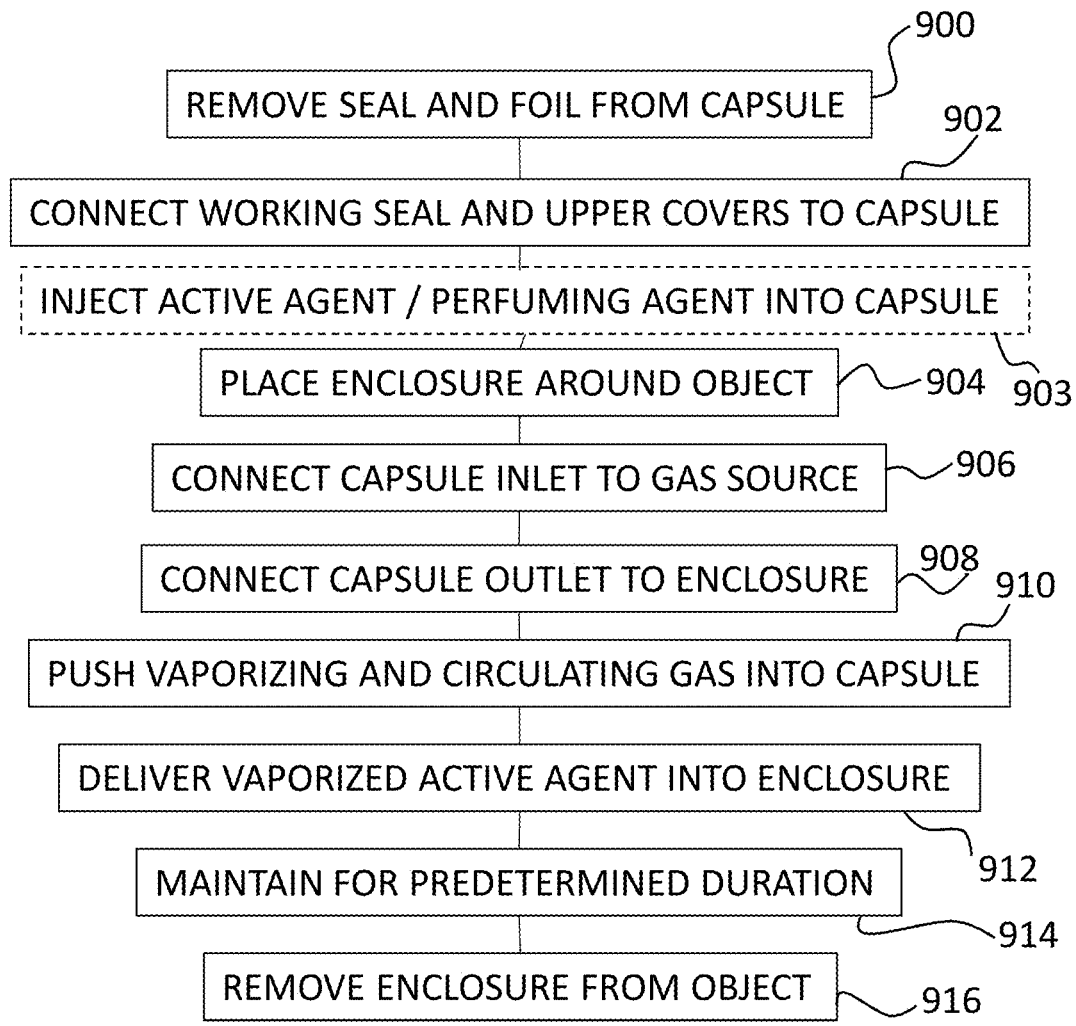
FIG. 11 is a flow chart of a method for treating an object with gas or vapor using the system of FIG. 10.

Reference is now made to FIG. 11, which is a flow chart of treating an object with gas or vapor using system 800 of FIG. 10, according to an exemplary embodiment of the teachings herein.

As seen in FIG. 11, initially the capsule is prepared for use, by removal of the sealing foil (32, FIG. 1A) and removable seal (30, FIGS. 4A-4F) at step 900, and connection of working seal (35, FIGS. 7A-7F), functional upper cover (40, FIGS. 5A-5F) and decorative upper cover (50, FIGS. 6A-6F) to the capsule body at step 902. In some embodiments, preparation of the capsule includes an additional step 903 of injecting the active agent and/or a perfuming agent, via elastomeric portions (230 and 232, FIG. 3G), into the capsule body.

At step 904 an enclosure is placed around an object to be treated, such as a cap being mounted on the head of a subject to be treated for lice and nits, so as to form an airtight volume around the object.

At step 906, the enclosure is attached to the outlet of the capsule, either directly or via one or more suitable connecting elements, such as a connecting tube. At step 908, an inlet of the capsule is connected to a gas source, such as vaporizing and circulating gas source 902 of FIG. 10, either directly or via one or more suitable connecting elements.

Steps 904, 906, and 908 need not necessarily be carried out in the order shown in FIG. 11, and may be carried out in any suitable order. For example, the capsule outlet may be connected to the enclosure before the enclosure is placed around the object.

Once the enclosure, capsule, and gas source are connected to one another, the system is ready for use. As such, at step 910, a predetermined volume of vaporizing and circulating gas is pushed into the capsule via the inlet to surround the substrate in the first volume (106, FIGS. 2A-2E) thereof, and to trigger vaporization of the active agent and/or the perfuming agent. A suitable volume of the vaporized active agent and/or perfuming agent together with the vaporizing and circulating gas is delivered, from the capsule outlet and into the enclosure, at step 912.

The vaporizing and circulating gas may be any suitable gas, such as ambient air, pure oxygen, pure carbon dioxide, or any other suitable gas, and need not necessarily include water vapor.

The enclosure is maintained on or around the object to the treated, such as the subject's head, for a predetermined duration, at step 914. Subsequently, at step 916, the enclosure is removed from the object, and the treatment is complete.

In some embodiments, for example when treating the subject's head for lice using a suitable concentration and volume of acetic acid vapor, the cap (enclosure) may be maintained on the subject's head for a duration in the range of 5 minutes to 15 minutes. In embodiments in which the treatment is used for another object, the treatment volume may be maintained surrounding the object for a duration in the range of 5 minutes to 4 hours.

As discussed hereinabove, the system and method described herein are suitable for treatment of many objects by provision of a vaporized active agent via an inlet and an outlet disposed on a single side of a vaporizing capsule. All such embodiments are considered to be within the scope of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

The invention claimed is:

1. A vaporization capsule, comprising:
   an elongate capsule body disposed along a longitudinal axis, including:
   a first wall defining a first volume;
   a second wall disposed about said first wall, and defining a second volume between an inner surface of said second wall and an outer surface of said first wall;
   a third wall disposed transversely to said longitudinal axis, said third wall extending radially inward from the inner surface of said second wall to define a third volume and engaging said first wall at an upper end thereof;
   at least one first bore extending through said third wall, and enabling fluid flow between said third volume and said first volume; and
   at least one second bore extending through said third wall and enabling fluid flow between said second volume and said third volume; and
   a bottom cover sealingly engaging said elongate capsule body at a bottom end thereof, said bottom cover including:
   an exterior perimeter engaging a lower end of said second wall;
   an interior core having an outer surface engaging an interior surface of said first wall adjacent the bottom end thereof;
   a hollow defined between said exterior perimeter and said outer surface of said interior core; and
   at least one indentation formed in said interior core, fluidly connecting said first volume and said second volume via said hollow,
   such that a fluid flow path extends from said at least one first bore to said at least one second bore, via said first volume, said at least one indentation, said hollow, and said second volume.

2. The vaporization capsule of claim 1, further comprising a first substrate disposed within said first volume, said first substrate adapted to have a liquid active agent absorbed therein or adsorbed thereto.

3. The vaporization capsule of claim 2, wherein said first substrate is further adapted to have a liquid perfuming agent absorbed therein or adsorbed thereto.

4. The vaporization capsule of claim 2, further comprising a second substrate disposed within said second volume, said second substrate being adapted to have a liquid perfuming agent absorbed therein or adsorbed thereto.

5. The vaporization capsule of claim 2, wherein said first substrate comprises a porous substrate.

6. The vaporization capsule of claim 2, further comprising said liquid active agent absorbed in or adsorbed to said first substrate.

7. The vaporization capsule of claim 3, further comprising said liquid perfuming agent absorbed in or adsorbed to said first substrate.

8. The vaporization capsule of claim 1, further comprising a seal adapted to be seated within said third volume, so as to seal said at least one first bore and said at least one second bore.

9. The vaporization capsule of claim 1, further comprising an upper cover adapted to engage said capsule body at an upper end thereof opposite said bottom end, said second cover including:
   an inlet in fluid communication with said first volume via said at least one first bore; and
   an outlet in fluid communication with said second volume via said at least one second bore,
   such that a fluid flow path exists from said inlet to said outlet.

10. The vaporization capsule of claim 9, wherein said upper cover is in threaded engagement with said upper end of said capsule body.

11. The vaporization capsule of claim 9, wherein said inlet and said outlet are aligned along a straight line.

12. The vaporization capsule of claim 9, wherein said inlet and said outlet are disposed at an angle relative to one another.

13. A method of vaporizing an active agent absorbed in or adsorbed to a first substrate disposed within the first volume of the capsule of claim 9, the method comprising:
   providing a first gas flow into said first volume via said inlet, said first gas flow vaporizing at least part of said active agent from said first substrate; and
   receiving a second gas flow including vapor of said active agent from said outlet, via said at least one indentation and said second volume.

14. A method of vaporizing an active agent absorbed in or adsorbed to a first substrate disposed within the first volume of the capsule of claim 8, the method comprising:
   removing said seal from said first volume;
   connecting an upper cover to said capsule body at an upper end thereof opposite said bottom end, said upper cover including:
   an inlet in fluid communication with said first volume via said at least one first bore; and
   an outlet in fluid communication with said second volume via said at least one second bore,
   providing a first gas flow into said first volume via said inlet, said first gas flow vaporizing at least part of said active agent absorbed into or adsorbed onto said first substrate in said first volume; and
   receiving a second gas flow including vapor of said active agent from said outlet, via said at least one indentation and said second volume.

15. A system for treatment of an object with an active agent, the system comprising:
   a vaporization capsule according to claim 9, the active agent being adsorbed onto or absorbed in said first substrate;
   a gas source, fluidly connected to said inlet of said vaporization capsule, and adapted to provide a gas stream into said first volume of said vaporization capsule via said inlet; and
   an enclosure, fluidly connected to said outlet of said vaporization capsule, and adapted to form an airtight volume around the object,
   wherein active agent vapor, vaporized by said gas stream in said first volume, is adapted to flow through said at least one indentation, said second volume, and said outlet into said airtight volume, thereby to treat the object.

16. A method for treating of an object with an active agent, using the vaporization capsule of claim 9, the method comprising:
- fluidly connecting a gas source to said inlet of said vaporization capsule;
- fluidly connecting an enclosure to said outlet of said vaporization capsule;
- using said enclosure, forming an airtight volume around the object to be treated; and
- activating said gas source so as to provide a gas stream into said first volume of said vaporization capsule via said inlet, said gas stream causing vaporization of at least part of said active agent in said first volume, and vapor of said active agent exiting said vaporization capsule via said outlet into said enclosure, so as to treat said object.

17. The method of claim 16, further comprising, prior to said fluidly connecting said gas source:
- removing a seal, sealing said at least one first bore and said at least one second bore, from said capsule body; and
- connecting said second cover to said capsule body, such that said inlet is in fluid communication with said at least one first bore and said outlet is in fluid communication with said at least one second bore.

18. The vaporization capsule of claim 4, wherein said second substrate comprises a porous substrate.

19. The vaporization capsule of claim 4, further comprising said liquid perfuming agent absorbed in or adsorbed to said second substrate.

* * * * *